United States Patent
North et al.

(10) Patent No.: US 10,407,504 B2
(45) Date of Patent: Sep. 10, 2019

(54) ANTAGONISTS FOR ABDOMINAL VASOPRESSIN V2 RECEPTOR AND USES THEREOF

(71) Applicant: Woomera Therapeutics, Inc, Lebanon, NH (US)

(72) Inventors: William G. North, Hanover, NH (US); Roy H. L. Pang, Etna, NH (US)

(73) Assignee: Woomera Therapeutics, Lebanon, NH (US)

(*) Notice: Subject to any disclaimer, the term of this patent is extended or adjusted under 35 U.S.C. 154(b) by 0 days.

(21) Appl. No.: 15/291,597

(22) Filed: Oct. 12, 2016

(65) Prior Publication Data

US 2017/0107292 A1 Apr. 20, 2017

Related U.S. Application Data

(63) Continuation of application No. 14/274,999, filed on May 12, 2014, now abandoned, which is a continuation of application No. PCT/US2012/064348, filed on Nov. 9, 2012.

(60) Provisional application No. 61/559,004, filed on Nov. 11, 2011.

(51) Int. Cl.
| | |
|---|---|
| *C07K 16/28* | (2006.01) |
| *A61K 38/31* | (2006.01) |
| *C07K 16/26* | (2006.01) |
| *A61K 51/10* | (2006.01) |
| *C07K 14/47* | (2006.01) |
| *A61K 39/395* | (2006.01) |
| *A61K 45/06* | (2006.01) |
| *A61K 49/00* | (2006.01) |
| *C07K 7/06* | (2006.01) |
| *C07K 14/72* | (2006.01) |
| *G01N 33/574* | (2006.01) |
| *A61K 38/00* | (2006.01) |
| *A61K 39/00* | (2006.01) |

(52) U.S. Cl.
CPC .......... *C07K 16/2869* (2013.01); *A61K 38/31* (2013.01); *A61K 39/3955* (2013.01); *A61K 45/06* (2013.01); *A61K 49/0058* (2013.01); *A61K 51/1036* (2013.01); *A61K 51/1063* (2013.01); *A61K 51/1096* (2013.01); *C07K 7/06* (2013.01); *C07K 14/4703* (2013.01); *C07K 14/72* (2013.01); *C07K 16/26* (2013.01); *G01N 33/57492* (2013.01); *A61K 38/00* (2013.01); *A61K 2039/505* (2013.01); *A61K 2039/507* (2013.01); *C07K 2317/34* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,018,812 B2 | 3/2006 | Oakley et al. | |
| 2005/0019841 A1 | 1/2005 | Garman et al. | |
| 2007/0083334 A1* | 4/2007 | Mintz | G06F 19/24 702/19 |
| 2008/0050376 A1* | 2/2008 | North | A61K 47/48438 424/135.1 |
| 2009/0280138 A1* | 11/2009 | Harrop | C07K 14/4748 424/185.1 |
| 2011/0021440 A1 | 1/2011 | Martin et al. | |
| 2014/0341810 A1 | 11/2014 | North et al. | |

FOREIGN PATENT DOCUMENTS

| | | |
|---|---|---|
| EP | 2657336 A1 | 10/2013 |
| WO | WO-2009137113 A2 | 11/2009 |

OTHER PUBLICATIONS

Wong et al. Vasopressin V2 receptor antagonists. Cardiovascular Research 51: 391-402, 2001.*
North et al. Growth impairment of small-cell cancer by targeting pro-vasopressin with MAG-1 antibody. Front. Oncol.,4 (article 16): 1-7, Feb. 11, 2014.*
North et al. New Agents for Treatment of Recurrent Small-Cell Cancer: Tumor-Specific Abnormal Vasopressin V2 Receptor Antibodies (Internal Medicine Review, Jun. 2016).*
Bolignano et al., Aquaretic inhibits renal cancer proliferation: Role of vasopressin receptor-2 (V2-R). Urol Oncol. Nov.-Dec. 2010;28(6):642-7.
Fay et al., Evidence for expression of vasopressin V2 receptor mRNA in human lung. Peptides. 1996;17(3):477-81.
NCBI GenBank Accession No. AAB87678, vasopressin receptor type 2 [*Homo sapiens*] Dec. 1, 1997. 1 page.

(Continued)

*Primary Examiner* — Alana Harris Dent
(74) *Attorney, Agent, or Firm* — McCarter & English, LLP; Yu Lu

(57) ABSTRACT

Provided herein are antagonists or binding agents of an abnormal vasopressin receptor $V_2$ (e.g., $AbnV_2$), such as antibodies and antigen-binding portions thereof specific for the receptor, for identifying and targeting cancer cells expressing such abnormal vasopressin receptor $V_2$. Additionally provided are methods of using said antagonists or binding agents, for example, to image cancer cells or in biological samples, or diagnose cancers, both in vivo and in vitro. The antagonists or binding agents may also be used for treating patients suffering from a cancer expressing the abnormal vasopressin receptor $V_2$, such as small cell lung cancer (SCLC), breast cancer, or ovarian cancer.

13 Claims, 14 Drawing Sheets

Specification includes a Sequence Listing.

(56) References Cited

OTHER PUBLICATIONS

North et al., MCF-7 breast cancer cells express normal forms of all vasopressin receptors plus an abnormal V2R. Peptides. 1999;20(7):837-42.

Verbalis, Vasopressin V2 receptor antagonists. J Mol Endocrinol. Aug. 2002;29(1):1-9.

* cited by examiner

SCLC Cancer

Ovarian Cancer

Breast Cancer

Breast Cancer
Pancreatic Cancer
FIG. 12A
FIG. 12B
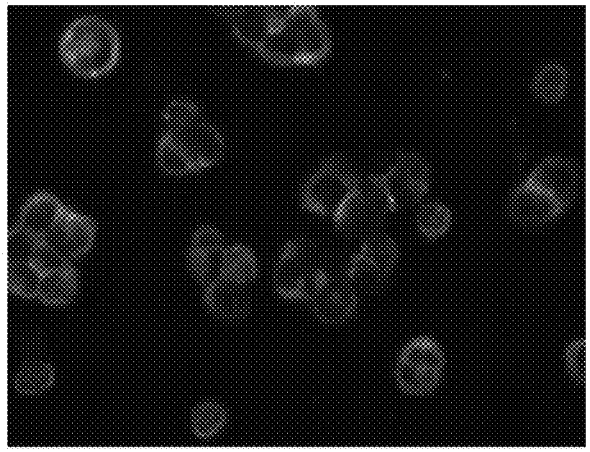
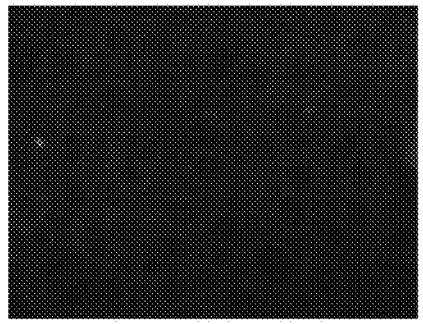
MCF-7
bxpc3
FIG. 12C
panc1

ANTAGONISTS FOR ABDOMINAL VASOPRESSIN V2 RECEPTOR AND USES THEREOF

REFERENCE TO RELATED APPLICATIONS

This application is a continuation application of U.S. Ser. No. 14/274,999, filed on May 12, 2014, which is a continuation application of International Application No. PCT/US2012/064348, filed on Nov. 9, 2012 and designated the U.S., and was published as WO 2013/071038, which International Application claims the benefit of the filing date of U.S. Provisional Application No. 61/559,004, filed on Nov. 11, 2011, the entire content of each of the above applications is incorporated herein by reference.

GOVERNMENT SUPPORT

The invention described herein may have been supported, in whole or in part, by the following grant from the National Institute of Health (NIH) of the U.S. Dept. of Health and Human Service (USHHS): 1-R43-CA162613-01. The U.S. government may have certain rights in the claimed invention.

BACKGROUND OF THE INVENTION

Small cell lung cancer (SCLC) is a fast-growing type of lung cancer, and it spreads much more quickly than non-small cell lung cancer. There are three different types of small cell lung cancer: small cell carcinoma (oat cell cancer), mixed small cell/large cell carcinoma, and combined small cell carcinoma. Most small cell lung cancers are the oat cell type.

About 15% of all lung cancer cases are small cell lung cancer. SCLC is the most aggressive form of lung cancer. It usually starts in the breathing tubes (bronchi) in the center of the chest. Although the cancer cells are small, they grow very quickly and create large tumors. These tumors often spread rapidly (metastasize) to other parts of the body, including the brain, liver, and bone. As a result, this type of cancer is very deadly. Only about 6% of people with SCLC survive 5 years after diagnosis.

Currently, there are about 40,000 new cases of SCLC patients per year. Present treatments of SCLC generally involve high-dose combination chemotherapy with or without radiation therapy [10-20]. Although there is a high initial response rate to these treatments, and long-term survival in up to 10% of all cases [19-20], average life expectancy is increased by only 8-15 months. While about 80% of these newly diagnosed SCLC patients respond to chemotherapy, remission generally lasts only 3-6 months. Unfortunately, there is no effective therapy to treat recurrent disease because it is resistant to available approaches, including chemotherapies. Therefore, a pressing need exists for new approaches for effective treatment that would provide long-term survival for SCLC patients.

Breast cancer is one of the leading causes of death among women throughout the world, and accounts for the death of approximately 50,000 women in the United States each year [8]. Although there have been many recent advances for effectively treating this disease [9], successful intervention still relies heavily on early detection through mammography and surgical removal. Therefore, a pressing need exists for a reliable and universal tumor marker system in breast cancer that could provide, advanced warnings of early post-oncogenic tissue changes, precise methods for identifying and evaluating changes in tumor burden and, additional new non-surgical methods of treatment that are effective in terms of providing long-term survival for patients.

Ovarian cancer is the fifth leading causes of death from cancer among women throughout the world, and accounts for the death of approximately 16,000 women in the United States each year (Young, *Gynecologic Malignancies* in J. N. Jameson, D. L. Kasper, T. R. Harrison, E. Braunwald, A. S. Fauci, S. L. Hauser, D. L. Longo (eds) *Harrison's Principles of Internal Medicine,* 16th Edition, McGraw-Hill, New York, N.Y., 2005). Although there have been many recent advances for effectively treating this disease (Goff et al., "Ovarian carcinoma diagnosis," *Cancer* 89: 2068-2075, 2000; Chobanian and Dietrich, "Ovarian Cancer," *Surg. Clin. North Amer.* 88:285-299, 2008), successful intervention still relies heavily on early detection and surgical removal. Therefore, a pressing need exists for the development of new non-surgical methods of treatment that are effective in terms of providing long-term survival for patients, and precise methods for identifying and evaluating changes in tumor burden.

The expression of the vasopressin gene is largely restricted to hypothalamic neurons, and it encodes for a protein product of ~17 kDa, to which an N-glycosidic side-chain of ~4 kDa is added, resulting in the ~20 kDa provasopressin (pro-VP) precursor. This protein is normally packaged into secretory vesicles where it undergoes enzymatic cleavage to generate vasopressin (VP), VP-associated neurophysin (VP-NP), and VP-associated glycopeptide (VAG) (North, W. G. In: D. Gash and G. Boer (eds.), *Vasopressin: Principles and Properties,* pp. 175-209. New York: Plenum Press, 1987). These components are then secreted into the circulation.

SUMMARY OF THE INVENTION

The invention described herein provides methods and compositions for treating tumors/cancers expressing a tumor-specific abnormal vasopressin $V_2$ receptor (such as $AbnV_2$). Treatable tumors/cancers include small-cell lung cancer (SCLC), especially recurrent SCLC, breast cancer, and ovarian cancer. The invention is partly based on the discovery that most such cancers (e.g., recurrent SCLC and primary SCLC) need to produce vasopressin and vasopressin receptors, and the abnormal vasopressin receptor $V_2$ presents a unique target specific for cancer cells, which target is useful both for diagnosis (such as imaging) purpose and therapeutic uses.

Particularly in the case of recurrent SCLC, the invention described herein provides a new pathway to effectively treat this otherwise treatment-resistant disease, thus significantly increasing long-term survival for patients with this otherwise treatment-refractory condition. In addition, since the same tumor-specific marker is expressed by primary and metastatic SCLC, this targeted approach could also have application to a larger population of patients.

While not wishing to be bound by any particular theory, anti-abnormal vasopressin $V_2$ receptor (such as $AbnV_2$) agents, such as antibodies against $AbnV_2$, maybe used as targeting agents directed against tumor-specific antigens of known structure and genetic origin that are not lost through antigenic modulation. Especially with respect to recurrent small-cell lung cancer, $AbnV_2$ is one of the few tumor antigens that seems to satisfy these criteria. Since $AbnV_2$ may be inactive as a vasopressin receptor, it is conceivable that effective treatments might require the attachment to the targeting antibody of a toxic label, such as $^{90}$Yttrium.

However, it is also possible, through ADCC, receptor hetero-dimerizations, internalization and initiation of apoptosis pathways, or alternate mechanisms, antibodies against the antigen could inhibit tumor growth in its native form.

An exemplary anti-abnormal vasopressin $V_2$ receptor (such as $AbnV_2$) agent is a monoclonal anti-$AbnV_2$ antibody directed against an extracellular tumor-unique C-terminal fragment of $AbnV_2$. The monoclonal antibody may be used as an effective targeting agent to facilitate safe treatment of the disease with few side-effects, and to increased long-term survival, particularly in patients with recurrent SCLC. On the other hand, the anti-abnormal vasopressin $V_2$ receptor (such as $AbnV_2$) agent may also be used as imaging agent to detect the presence and/or measure the quantity of the target antigen, thus serving as a tumor-/cancer-specific diagnostic tool.

Thus provided herein are antagonists, primarily (but not exclusively) antibodies and antigen-binding portions thereof, for abnormal vasopressin $V_2$ receptor-expressing cancer cells. Additionally provided herein are methods of using said antagonists, for example, to image cancer cells in vivo and/or in biological samples in vitro. Said antagonists may also be used for treating patients suffering from an abnormal vasopressin $V_2$ receptor-expressing cancer or tumor, such as SCLC (including the recurrent SCLC), breast cancer, or ovarian cancer.

More specifically, in one respect, the invention provides a method of treating a tumor or a cancer in a patient expressing an abnormal vasopressin receptor $V_2$ in the tumor or cancer (or killing tumor/cancer cells expressing an abnormal vasopressin receptor $V_2$, or inhibiting the proliferation and/or growth of tumor/cancer cells expressing an abnormal vasopressin receptor $V_2$), the method comprising administering a therapeutically effective amount of an antagonist or a binding agent specific for the abnormal vasopressin receptor $V_2$ to the patient in need thereof, wherein the abnormal vasopressin receptor $V_2$ lacks a functional $7^{th}$ transmembrane region of the wild-type vasopressin receptor $V_2$, and has a C-terminus exposed on extracellular surface of cells of the tumor/cancer.

In certain embodiments, the abnormal vasopressin receptor $V_2$ is $AbnV_2$, which comprises the most C-terminal six residues of SEQ ID NO: 1 fused to the C-terminus of a truncated wildtype human vasopressin receptor $V_2$ ending at residues 302 and 303 (Leu-Glu). See SEQ ID NO: 4. In a related aspect, the invention relates to the abnormal vasopressin receptor $V_2$ described herein, or any natural or synthetic variants thereof that comprise the same six C-terminal residues and at least about 90%, 92%, 95%, 97%, 99%, 99.3%, 99.7% overall sequence identity with the abnormal vasopressin receptor $V_2$ described herein.

In certain embodiments, the cancer is small cell lung cancer (SCLC), breast cancer, or ovarian cancer. In certain embodiments, the SCLC cancer is a recurrent SCLC. In certain embodiments, the breast cancer is an invasive breast cancer, a triple-negative breast cancer (estrogen receptor-negative, progesterone receptor-negative, and HER2-negative), a ductal and lobular breast tumor, or a DCIS. In certain embodiments, the tumor is a breast tissue hyperplasia (such as Atypical Ductal Hyperplasia (ADH)).

In certain embodiments, the antagonist or binding agent is an antibody or an antigen-binding portion thereof.

In certain embodiments, the antibody or an antigen-binding portion thereof binds to the exposed C-terminus of the abnormal vasopressin $V_2$ receptor, such as the peptide of SEQ ID NO: 1, or the most C-terminal six residues of SEQ ID NO: 1.

In certain embodiments, the antibody is a mouse antibody, a human antibody, a mouse-human chimeric antibody, or a humanized antibody.

In certain embodiments, the antigen-binding portion is scFv, Fab, F(ab')$_2$, Fd, Fv, or dAb.

In certain embodiments, the method further comprises administering an effective amount of a pharmaceutical composition comprising a chemotherapeutic agent effective for treating the cancer. The pharmaceutical composition may further comprise epinephrine.

In certain embodiments, the binding agent and the pharmaceutical composition are administered concomitantly. In certain embodiments, the binding agent and the pharmaceutical composition are administered in a single formulation. In certain embodiments, the binding agent and the pharmaceutical composition are administered as separate formulations.

In certain embodiments, the method further comprises administering an effective amount of a pharmaceutical composition comprising at least one of dexamethasone, IBMX, 8-bromoadenosine 3',5'-cyclic monophosphate (8br-cAMP), cyclophosphamide, cisplatin, etoposide VP-16 and forskolin.

In certain embodiments, the method further comprises performing surgical removal of at least one tumor or cancer from the patient.

In certain embodiments, the method further comprises performing radiation therapy.

In certain embodiments, the method further comprises administering a somatostatin analogue.

In certain embodiments, the method further comprises administering at least one of imatinib, sunitinib, temozolide, thalidomide, sorafenib, and panitumumab.

In certain embodiments, the antibody or antibody-binding portion thereof comprises a label, such as a fluorescent label, a radiolabel, a toxin, a metal compound, and biotin.

In certain embodiments, the fluorescent label is selected from the group consisting of Texas Red, phycoerythrin (PE), cytochrome c, and fluorescent isothiocyanate (FITC).

In certain embodiments, the radiolabel is selected from the group consisting of $^{32}P$, $^{33}P$, $^{43}K$, $^{47}Sc$, $^{52}Fe$, $^{57}Co$, $^{64}Cu$, $^{67}Ga$, $^{67}Cu$, $^{68}Ga$, $^{71}Ge$, $^{75}Br$, $^{76}Br$, $^{77}Br$, $^{77}As$, $^{77}Br$, $^{81}Rb/^{81m}Kr$, $^{87m}Sr$, $^{90}Y$, $^{97}Ru$, $^{99}Tc$, $^{100}Pd$, $^{101}Rh$, $^{103}Pb$, $^{105}Rh$, $^{109}Pd$, $^{111}Ag$, $^{111}In$, $^{113}In$, $^{119}Sb$, $^{121}Sn$, $^{123}I$, $^{125}I$, $^{127}Cs$, $^{128}Ba$, $^{129}Cs$, $^{131}I$, $^{131}Cs$, $^{143}Pr$, $^{153}Sm$, $^{161}Tb$, $^{166}Ho$, $^{169}Eu$, $^{177}Lu$, $^{186}Re$, $^{188}Re$, $^{189}Re$, $^{191}Os$, $^{193}Pt$, $^{194}Ir$, $^{197}Hg$, $^{199}Au$, $^{203}Pb$, $^{211}At$, $^{212}Pb$, $^{212}Bi$ and $^{213}Bi$.

In certain embodiments, the toxin is selected from the group consisting of ricin, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin.

Another aspect of the invention provides a method of killing a tumor or cancer cell expressing an abnormal vasopressin receptor $V_2$, the method comprising contacting the tumor/cancer cell with an antagonist or a binding agent specific for the abnormal vasopressin receptor $V_2$, wherein the abnormal vasopressin receptor $V_2$ lacks a functional $7^{th}$ transmembrane region of the wild-type vasopressin receptor $V_2$, and has a C-terminus exposed on extracellular surface of cells of the cancer.

Another aspect of the invention provides a method of inhibiting the growth of a tumor/cancer cell expressing an abnormal vasopressin receptor $V_2$, the method comprising contacting the tumor/cancer cell with an antagonist or a binding agent specific for the abnormal vasopressin receptor $V_2$, wherein the abnormal vasopressin receptor $V_2$ lacks a functional $7^{th}$ transmembrane region of the wild-type vasopressin receptor $V_2$, and has a C-terminus exposed on extracellular surface of cells of the cancer.

In certain embodiments, the abnormal vasopressin receptor $V_2$ is expressed on the surface of the cancer cell.

Another aspect of the invention provides a method of diagnosing the presence in a patient a tumor/cancer expressing an abnormal vasopressin receptor $V_2$, the method comprising: a) obtaining a biological sample (such as a biopsy) from the patient; b) if necessary, rendering the biological sample amenable to immunoassay; c) contacting the sample with an antibody or an antigen-binding portion thereof specific for the abnormal vasopressin receptor $V_2$, under conditions that allow for binding of the antibody or antigen-binding portion to the abnormal vasopressin receptor $V_2$; and d) determining if the cells of the sample expresses a significantly higher level of the abnormal vasopressin receptor $V_2$ compared to a control tissue; wherein the patient is diagnosed to have the cancer expressing the abnormal vasopressin receptor $V_2$ if the cells of the sample express a significantly higher level of the abnormal vasopressin receptor $V_2$ compared to the control tissue.

Another related aspect of the invention provides a method of identifying a patient suitable for treatment with the subject binding agent specific for an abnormal vasopressin receptor $V_2$, by diagnosing the presence in a patient a tumor/cancer expressing the abnormal vasopressin receptor $V_2$, the method comprising: a) obtaining a biological sample (such as a biopsy) from the patient; b) if necessary, rendering the biological sample amenable to immunoassay; c) contacting the sample with an antibody or an antigen-binding portion thereof specific for the abnormal vasopressin receptor $V_2$, under conditions that allow for binding of the antibody or antigen-binding portion to the abnormal vasopressin receptor $V_2$; and d) determining if the cells of the sample expresses a significantly higher level of the abnormal vasopressin receptor $V_2$ compared to a control tissue; wherein the patient is selected for treatment with the subject binding agent specific for the abnormal vasopressin receptor $V_2$ if the cells of the sample express a significantly higher level of the abnormal vasopressin receptor $V_2$ compared to the control tissue. Preferably, the method further comprises treating the identified/selected patient by administering to the patient one or more of the subject binding agent specific for the abnormal vasopressin receptor $V_2$, with or without a second therapy.

In certain embodiments, the method further comprises, if the biological sample expresses a significantly higher level of the abnormal vasopressin receptor $V_2$ compared to the control, administering a therapeutically effective amount of the antibody or antigen-binding portion thereof to the patient.

In certain embodiments, before step (a), the patient has been diagnosed as having a cancer expressing the abnormal vasopressin receptor $V_2$.

Another aspect of the invention provides a kit for screening a biological sample for a cancer expressing an abnormal vasopressin receptor $V_2$, the kit comprising an antibody or an antigen-binding portion thereof specific for the abnormal vasopressin receptor $V_2$, wherein the kit is labeled for use in detecting the cancer expressing the abnormal vasopressin receptor $V_2$.

Another aspect of the invention provides a method of detecting or imaging in a patient a tumor expressing an abnormal vasopressin receptor $V_2$, the method comprising: a) administering to the patient an antibody or an antigen-binding portion thereof specific for the abnormal vasopressin receptor $V_2$, wherein the antibody or antigen-binding portion thereof comprise a detectable label; b) detecting the label; and, c) determining the amount of the label in the patient compared to that of a control.

Another related aspect of the invention provides a method of identifying/selecting a patient suitable for treatment with the subject binding agent specific for the abnormal vasopressin receptor $V_2$, by detecting or imaging in a patient a tumor expressing an abnormal vasopressin receptor $V_2$, the method comprising: a) administering to the patient an antibody or an antigen-binding portion thereof specific for the abnormal vasopressin receptor $V_2$, wherein the antibody or antigen-binding portion thereof comprise a detectable label; b) detecting the label; and, c) determining the amount of the label in the patient compared to that of a control, wherein the patient is selected for said treatment when the amount of the label in the patient is significantly higher compared to that of the control. Preferably, the method further comprises treating the identified/selected patient by administering to the patient one or more of the subject binding agent specific for the abnormal vasopressin receptor $V_2$, with or without a second therapy.

In certain embodiments, the patient is diagnosed as having the tumor expressing the abnormal vasopressin receptor $V_2$, or having an enhanced risk of developing said tumor, if the amount of the detected label is significantly higher than that of the control.

In certain embodiments, the method further comprises administering a therapeutically effective amount of the antibody or antigen-binding portion thereof to the patient.

In certain embodiments, the patient has been diagnosed as having a cancer expressing the abnormal vasopressin receptor $V_2$.

In certain embodiments, before step (a), the patient has been diagnosed as having a small cell lung cancer (SCLC), a breast cancer, or an ovarian cancer.

In certain embodiments, the method further comprises determining the location and/or volume of a plurality of cells expressing the abnormal vasopressin receptor $V_2$.

The potential uses for methods of administering anti-abnormal vasopressin $V_2$ receptor antibodies and antigen-binding portions thereof are not limited to therapeutic use, but also includes basic research use. For example, the antibodies and portions thereof may be used in tissue culture or in a model organism to study the mechanism by which anti-abnormal vasopressin $V_2$ receptor antibodies inhibit cancer.

Another aspect of the invention provides an isolated polypeptide comprising the most C-terminal six residues of SEQ ID NO: 1.

In certain embodiments, the isolated polypeptide is a fusion protein comprising the most C-terminal six residues of SEQ ID NO: 1 fused to a heterologous protein.

In certain embodiments, the most C-terminal six residues of SEQ ID NO: 1 is fused to the C-terminus of the heterologous protein.

In certain embodiments, the isolated polypeptide is capable of being used as an antigen to produce an antibody specific for the most C-terminal six residues of SEQ ID NO: 1.

Another aspect of the invention provides an isolated abnormal vasopressin receptor $V_2$ (AbnV$_2$), having a sequence of SEQ ID NO: 4.

Another aspect of the invention provides an isolated polynucleotide encoding the subject isolated polypeptide.

Another aspect of the invention provides a vector comprising the subject polynucleotide.

Another aspect of the invention provides a cell comprising the subject isolated polynucleotide of the invention, or the subject vector of the invention.

It is contemplated that any embodiment of the invention can be combined with any other embodiment(s), including embodiment(s) described under different aspects of the invention.

BRIEF DESCRIPTION OF THE DRAWINGS

FIG. 4A: 6× alternate daily treatment with 50 µg/25 gm bw Ab. FIG. 4B: 15× daily treatment with 100 µg/25 bw Ab.

FIGS. 12A-12C show Abner confocal analysis result.

(FIG. 13A) Treatments with 3 mg/kg bw MOPC21 daily, and 3 mg/kg bw Abner daily (p<0.03); (FIG. 13B) Six treatments on alternating days with 50 µCi $^{90}$Yttrium-labelled MOPC21, and 50 µCi $^{90}$Yttrium-labelled Abner (p<0.007).

DETAILED DESCRIPTION

1. Overview

Figure 1:
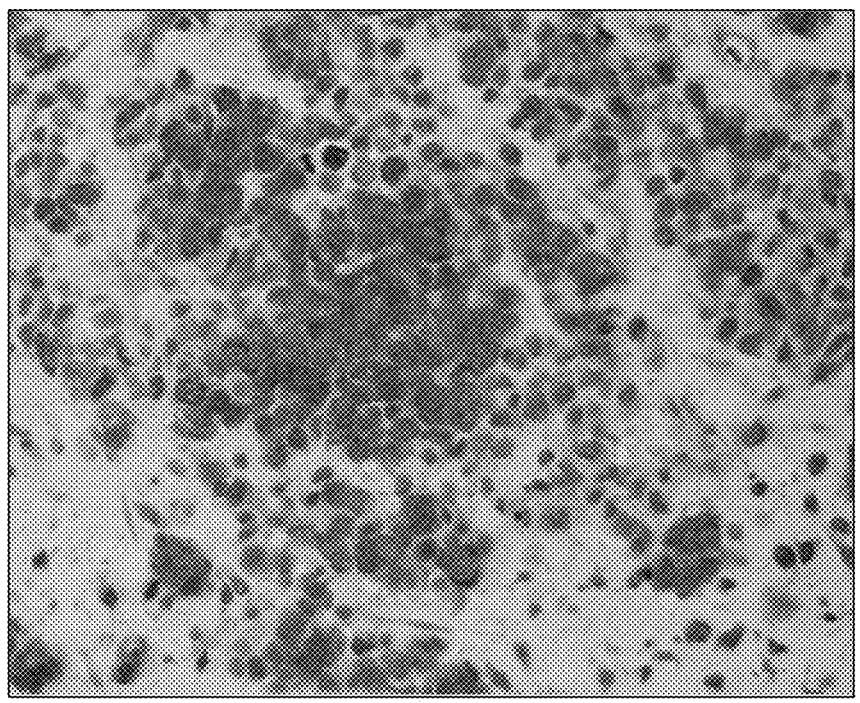
FIG. 1 is a representative immunohistochemistry (IHC) image of small cell lung cancer (SCLC) sample stained with anti-AbnV$_2$ antibody.

The invention is partly based on the "STEPS" concept of neuropeptide/receptor production by tumors, which emphasizes process over origin, and thus serves as a counterbalance to the APUD concept of Pierce. Here, STEPS refers to Selective Tumor gene Expression of Peptides/receptors essential for Survival, and points to the now generally recognized "autocrine growth loop" involving peptides as a key survival strategy of these tumors.

Vasopressin is one such peptide. It is expressed by recurrence small-cell lung cancer together with all four vasopressin receptors. Notably, while three of these receptors ($V_{1a}$, $V_{1b}$, and hVACM) are all normal and functional there is an abnormal splicing of the mRNA for vasopressin $V_2$ receptor, resulting in the formation of a tumor-specific non-functional truncated receptor that lacks the seventh trans-membrane region, and has a unique extracellular C-terminal tail (see the last six residues of SEQ ID NO: 1, and SEQ ID NO: 4). This abnormally spliced molecule is referred to herein as "AbnV$_2$."

It should be note that other abnormal vasopressin $V_2$ receptor similar to AbnV$_2$ may also be present in cancers, such as SCLC, breast cancer, and ovarian cancer. These other abnormal receptors, though not identical to AbnV$_2$, may share certain important structural features with AbnV$_2$, such as lacking a functional 7$^{th}$ transmembrane region, and/or having an exposed C-terminus on the extracellular surface. These other abnormal vasopressin $V_2$ receptors are also within the scope of the invention. In certain embodiments, variant abnormal vasopressin $V_2$ receptors may comprise the same six C-terminal residues and at least about 90%, 92%, 95%, 97%, 99%, 99.3%, 99.7% overall sequence identity with the abnormal vasopression receptor $V_2$ described herein.

Applicants have shown here that antagonists of abnormal vasopressin $V_2$ receptor (e.g., AbnV$_2$ antagonists), such as antibodies directed against the unique C-terminus of the protein expressed on the surface of certain cancer cells, including recurrent SCLC, breast cancer, and ovarian cancer, can effectively detect such cancer cells for diagnosis purpose, and can also effectively target such cancer cells for therapy.

There are various antagonists specifically targeting the C-terminus of the abnormal vasopressin $V_2$ receptor may be available. In a preferred embodiment, the antagonist is an antibody or an antigen-binding portion hereof that specifically bind the C-terminus of the abnormal vasopressin $V_2$ receptor, such as Abner1 (see below).

The descriptions in the sections below provide more details concerning the different aspects of the invention, which aspects may be combined with one another without restriction unless explicitly disclaimed.

2. Definitions

As used herein, "abnormal vasopressin $V_2$ receptor" includes a vasopressin $V_2$ receptor that lacks a functional 7$^{th}$ transmembrane region of the wild-type vasopressin receptor $V_2$, and has a C-terminus exposed on extracellular surface of cells that express such abnormal receptor, such as certain cancer cells (e.g., SCLC cells, breast cancer cells, or ovarian cancer cells).

An exemplary abnormal vasopressin $V_2$ receptor is AbnV$_2$, which is encoded by an abnormal splicing variant of the mRNA for vasopressin $V_2$ receptor. AbnV$_2$ is a tumor-specific non-functional truncated receptor that lacks the seventh trans-membrane region and has a unique extracellular C-terminal tail. Antibodies directed against the unique C-terminus of AbnV$_2$ reveal that the abnormal receptor is expressed on the extracellular surface of cancer cells, such as recurrent SCLC as an available target. The sequence of the AbnV$_2$ protein comprises the last (most C-terminal) six residues of SEQ ID NO: 1 fused to the C-terminus of a truncated wildtype vasopressin receptor $V_2$ (UniProtKB/

Swiss-Prot access No. P30518 (V2R_HUMAN)) ending at residues 302 and 303 (Leu-Glu). See SEQ ID NO: 4 below, with the most C-terminal six residues of SEQ ID NO: 1 in bold type.

(SEQ ID NO: 4)
MLMASTTSAV PGHPSLPSLP SNSSQERPLD TRDPLLARAE
LALLSIVFVA VALSNGLVLA ALARRGRRGH WAPIHVFIGH
LCLADLAVAL FQVLPQLAWK ATDRFRGPDA LCRAVKYLQM

VGMYASSYMI LAMTLDRHRA ICRPMLAYRH GSGAHWNRPV
LVAWAFSLLL SLPQLFIFAQ RNVEGGSGVT DCWACFAEPW
GRRTYVTWIA LMVFVAPTLG IAACQVLIFR EIHASLVPGP
SERPGGRRRG RRTGSPGEGA HVSAAVAKTV RMTLVIVVVY
VLCWAPFFLV QLWAAWDPEA PLEGGCSRG

The genomic sequence (including intron sequence) encoding polypeptide of SEQ ID NO: 4 is set forth below.

(SEQ ID NO: 5)
```
   1  atgctcatgg cgtccaccac ttccggtaag gcttgcccct ccatgagtcc ggtgggcaga
  61  gtgggtttga cgattcaggg aagcccctct ttctaaagac ctccttcacc ctcacctctg
 121  ggtgtgtctc tccaggctgc caatgagtgg ggaggggagc acagcccac ttccccgcca
 181  gggctggggc tggggctggg gctggggctg ccctccttc tggactgcat gagcctgggg
 241  tgtgtatccc tcataacatg gctttcctgg agtcccctct gctaggagcc aggaagtggg
 301  tgtccggatg ggggcacggg aggcaggcct gagtccccct gcacagcacc ctctctaacc
 361  aggccctctt cccgactcct tcccagctgt gcctgggcat ccctctctgc ccagcctgcc
 421  cagcaacagc agccaggaga ggccactgga cacccggac ccgctgctag cccgggcgga
 481  gctggcgctg ctctccatag tctttgtggc tgtggccctg agcaatggcc tggtgctggc
 541  ggccctagct cggcggggcc ggcggggcca ctgggcaccc atacacgtct tcattggcca
 601  cttgtgcctg gccgacctgg ccgtggctct gttccaagtg ctgccccagc tggcctggaa
 661  ggccaccgac cgcttccgtg gccagatgc cctgtgtcgg ccgtgaagt atctgcagat
 721  ggtgggcatg tatgcctcct cctacatgat cctggccatg acgctggacc gccaccgtgc
 781  catctgccgt cccatgctgg cgtaccgcca tggaagtggg gctcactgga accggccggt
 841  gctagtggct tgggccttct cgctccttct cagcctgccc cagctcttca tcttcgccca
 901  gcgcaacgtg gaaggtggca gcggggtcac tgactgctgg gcctgctttg cggagccctg
 961  gggccgtcgc acctatgtca cctggattgc cctgatggtg ttcgtggcac ctaccctggg
1021  tatcgccgcc tgccaggtgc tcatcttccg ggagattcat gccagtctgg tgccagggcc
1081  atcagagagg cctgggggc gccgcagggg acgccggaca ggcagccccg gtgagggagc
1141  ccacgtgtca gcagctgtgg ccaagactgt gaggatgacg ctagtgattg tggtcgtcta
1201  tgtgctgtgc tgggcaccct tcttcctggt gcagctgtgg gccgcgtggg acccggaggc
1261  acctctggaa ggtGGGTGTA GCCGTGGCta ggctgacgg ggccacttgg gcttggccgc
1321  atgcccctgt gccccaccag ccatcctgaa cccaacctag atcctccacc tccacagggg
1381  cgcccttgt gctactcatg ttgctggcca gcctcaacag ctgcaccaac ccctggatct
1441  atgcatcttt cagcagcagc gtgtcctcag agctgcgaag cttgctctgc tgtgcccggg
1501  gacgcacccc acccagcctg ggtccccaag atgagtcctg caccaccgcc agctcctccc
1561  tggccaagga cacttcatcg tga
```

In SEQ ID NO: 5, nucleotides 1272 and 1273 (GT) are the intron 5' splice signal. The immediately following 15 capitalized nucleotides (nt 1274-1288) are intron sequences encoding the five most C-terminal amino acids of SEQ ID NOs: 1 and 4. Nucleotides 1265-1273 encodes the three immediately preceding residues Leu (L), Glu (E), and Gly (G). The double underlined sequence TAG terminates translation of the intron sequence.

It should be noted, however, abnormal vasopressin $V_2$ receptor is not limited to $AbnV_2$. Other similar mutations, especially those similar to $AbnV_2$, preferably identical in the most C-terminal six residues, may also be present in cancers, such as SCLC, breast, and ovarian cancer.

"Administering," "administration," or other grammatical variations is defined herein as providing a composition to a patient in a manner that results in the composition coming into contact with the patient's body, in a manner that permits or leads to a desired therapeutic effect. Such an administration can be by any route, including, without limitation, subcutaneous, intradermal, intravenous, intra-arterial, intraperitoneal, intramuscular, and/or topical.

The term "amino acid residue" is known in the art. In general, the abbreviations used herein for designating the amino acids and the protective groups are based on recommendations of the IUPAC-IUB Commission on Biochemical Nomenclature (see *Biochemistry* (1972) 11:1726-1732). In certain embodiments, the amino acids used are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan. In other embodiments, an amino acid may be modified by post-translational modifications, such as glycosylation, phosphorylation, deamidation, isomerization, pyroglutamic acid modification, and oxidation (e.g., methionine oxidation).

As used herein, the term "antibody" refers to an immunoglobulin molecule. The term "antibody" encompasses monoclonal and polyclonal antibodies. The antibody may be an IgG, an IgM, an IgE, an IgA or an IgD molecule. In certain embodiments, the antibody is an IgG and is an IgG1, IgG2, IgG3 or IgG4 subtype. The class and subclass of antibodies may be determined by any method known in the art, for example, by using antibodies that are specific for a particular class and subclass of antibody. Such antibodies are available commercially. The class and subclass can be determined by ELISA or Western blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

As used herein, the term "antibodies" encompasses isolated immunoglobulins produced in vivo, as well as those produced in vitro by, for example, a hybridoma, and antigen binding fragments (e.g., Fab' preparations) of such immunoglobulins, as well as to recombinantly expressed antigen binding proteins, including immunoglobulins, chimeric immunoglobulins, "humanized" immunoglobulins such as COMPOSITE HUMAN ANTIBODIES™ immunoglobulins, antigen binding portions of such immunoglobulins, single chain antibodies, and other recombinant proteins containing antigen binding domains derived from immunoglobulins. As used herein, in certain embodiments, "antibodies" also include antigen binding synthetic peptides comprising sequences derived from the sequences of immunoglobulin antigen binding domains. In other embodiments, "antibodies" exclude such antigen binding synthetic peptides. In some embodiments, the anti-$AbnV_2$ antibody or antigen-binding portion thereof contains non-natural amino acid residues and/or is conjugated to additional molecules such as PEG.

The term "human antibody," as used herein, is intended to include antibodies having variable and constant regions obtained or derived from human germline immunoglobulin sequences. The human antibodies of the invention may include amino acid residues not encoded by human germline immunoglobulin sequences or sequences of actual human DNA (e.g., human antibodies of the invention may include amino acid mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor, L. D., et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody," as used herein, is intended to refer to an antibody that is substantially free of other antibodies having different antigenic specificities, e.g., an isolated antibody that specifically binds abnormal vasopressin $V_2$ receptor is substantially free of antibodies that specifically bind antigens other than the abnormal vasopressin $V_2$ receptor, including the wild-type vasopressin $V_2$ receptor. An isolated antibody that specifically binds abnormal vasopressin $V_2$ receptor (e.g., one that specifically binds the unique C-terminal 7 residues in the abnormal vasopressin $V_2$ receptor described herein) may, however, have cross-reactivity to other antigens, such as the corresponding abnormal vasopressin $V_2$ receptor molecules from other species. Moreover, an isolated antibody may be substantially free of other cellular material and/or chemicals.

As used herein, the "antigen-binding portion thereof" of an anti-Abn$V_2$ antibody refers to a portion of an anti-Abn$V_2$ antibody that binds to its antigen Abn$V_2$ with substantial affinity. Substantial affinity includes affinity that is at least 1/100, 1/50, 1/20, 1/10, 1/5, or 1/2 the affinity of the (native) antibody for AbnV$_2$. Antigen-binding portions may be produced by recombinant DNA techniques or by enzymatic or chemical cleavage of intact antibodies. Antigen-binding portions include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide.

As used herein, "biological sample" refers to a sample taken from the body of a patient. Such samples include tissue biopsy sample, blood samples, urine samples, and the like.

As used herein, the term "cancer" refers to a condition in which a cell in a patient's body undergoes abnormal, uncontrolled proliferation. "Cancer" also refers to cancerous or malignant tumor tissues. In certain embodiments, the cancer is malignant. Non-limiting examples of cancers include SCLC, breast cancer, ovarian cancer.

As used herein, the term "tumor" is used to mean a condition in which a cell in a patient's body undergoes abnormal, uncontrolled proliferation. In certain embodiments, the tumor is malignant. In certain embodiments, the tumor is benign. Non-limiting example of tumor include hyperplasia.

"Homology" is a measure of the identity of nucleotide sequences or amino acid sequences. In order to characterize the homology, subject sequences are aligned so that the highest percentage homology (match) is obtained, after introducing gaps, if necessary, to achieve maximum percent homology. N- or C-terminal extensions shall not be construed as affecting homology. "Identity" per se has an art-recognized meaning and can be calculated using published techniques. Computer program methods to determine identity between two sequences, for example, include DNAStar® software (DNAStar Inc. Madison, Wis.); the GCG® program package (Devereux, J., et al. *Nucleic Acids Research* (1984) 12(1): 387); BLASTP, BLASTN, FASTA (Atschul, S. F. et al., *J. Molec. Biol.* (1990) 215: 403). Homology (identity) as defined herein is determined conventionally using the well-known computer program, BESTFIT® (Wisconsin Sequence Analysis Package, Version 8 for Unix, Genetics Computer Group, University Research Park, 575 Science Drive, Madison, Wis., 53711). When using BESTFIT® or any other sequence alignment program (such as the Clustal algorithm from MegAlign software (DNASTAR®) to determine whether a particular sequence is, for example, about 90% homologous to a reference sequence, the parameters are set such that the percentage of identity is calculated over the full length of the reference nucleotide sequence or amino acid sequence and that gaps in homology of up to about 90% of the total number of nucleotides in the reference sequence are allowed.

A "humanized" antibody or antigen-binding portion thereof, as used herein, is an antibody originally generated in a non-human animal, where the non-human animal content (especially the portion not directly responsible for antigen-binding, e.g., the non-CDR region) has been reduced or replaced by corresponding human sequence, by altering the original amino acid sequence, or a fragment of the antibody. The non-human animal content may be less than 50%, 40%, 30%, 20%, 10%, or 5%. In certain humanized antibodies, the six CDRs of the heavy and light chains and a limited number of structural amino acids of the murine monoclonal antibody are grafted by recombinant technology to the CDR-depleted human IgG scaffold. A humanized antibody may also be a fully human antibody, which may be made in humanized mice resulting in antibodies that do not contain any mouse sequences. In certain embodiments, chimeric, humanized or primatized (CDR-grafted) antibodies, comprising portions derived from different species or fully human antibodies, are also encompassed by the present disclosure. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023; Boss et al., U.S. Pat. No. 4,816,397; Boss et al., European Patent No. 0,120,694; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., *BioTechnology*, 10: 1455-1460 (1992), regarding primatized antibody. See, e.g., Ladner et al., U.S. Pat. No. 4,946,778; and Bird, R. E. et al., *Science*, 242: 423-426 (1988)), regarding single chain antibodies.

As used herein, the term "inappropriately express" refers to substantial expression of a gene (or protein) that occurs in a cell type that does not ordinarily substantially express that gene (or protein). For example, provasopressin is normally expressed only in the hypothalamus, so substantial expression of provasopressin outside the hypothalamus is considered inappropriate expression of provasopressin. In certain embodiments, when the expression difference is quantitative, the expression levels are preferably statistically significantly different (e.g., $p<0.05$, or $p<0.01$).

As used herein, the term "label" or "labeled" refers to incorporation of another molecule in the antibody, antigen-binding portion thereof, or peptide. In one embodiment, the label is a detectable marker, e.g., incorporation of a radiolabeled amino acid. Various methods of labeling polypeptides and glycoproteins are known in the art and may be used. Examples of labels for polypeptides include, but are not limited to, the following: radioisotopes or radionuclides, fluorescent labels, enzymatic labels, chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, and toxins.

"MAG-1" as used herein refers to the monoclonal antibody that is produced by the hybridoma having ATCC Number PTA-5322.

"Abner" or "mAbner" as used herein refers to the mouse monoclonal antibody that is produced by the mouse hybridoma having ATCC Number PTA-125592, deposited on Dec. 21, 2018 under the provisions of the Budapest Treaty, at the American Type Culture Collection (ATCC®), Manassas, Va., USA.

A "patient" or "subject" to be treated by the subject methods may mean either a human or non-human animal, such as primates, mammals, vertebrates, rodents, etc.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient, within a reasonable risk-benefit ratio. In certain embodiments, a pharmaceutically acceptable carrier is non-pyrogenic.

As used herein, "provasopressin-binding antibody" refers to an antibody that binds provasopressin with high affinity. Exemplary provasopressin-binding antibodies include MAG-1 (described in US Application Publication No. 2008-0050376 and produced by the hybridoma having ATCC Number PTA-5322), and the closely related antibodies MAG-2, MAG-3, MAG-4, and MAG-5 (see U.S. Provisional Application 61/127,089 and PCT publication WO 2009/137113A2, which are both incorporated herein by reference in their entirety). In certain embodiments, the provasopressin-binding antibodies include Boris and humanized antibodies derived from Boris. In certain embodiments, the provasopressin-binding antibodies include antibodies having CDR-H3 and CDR-L3 regions identical to that of any one of MAG-1, MAG-2, MAG-3, MAG-4, or MAG-5. In certain embodiments, the provasopressin-binding antibodies include antibodies having CDR-H1, CDR-H2, CDR-H3, CDR-L1, CDR-L2, and CDR-L3 regions identical to that of any one of MAG-1, MAG-2, MAG-3, MAG-4, or MAG-5. In certain embodiments, the provasopressin-binding antibodies include antibodies having LCVR (light chain variable region) and HLVR (heavy chain variable region) identical to that of any one of MAG-1, MAG-2, MAG-3, MAG-4, or MAG-5. In certain embodiments, the provasopressin-binding antibodies include antibodies having a single Ala substitution in any one of the CDR3 residues in the light chain and/or heavy chain sequence of any one of MAG-1, MAG-2, MAG-3, MAG-4, or MAG-5. In certain embodiments, the provasopressin-binding antibodies include antibodies having 2, 3, 4, or 5 Ala substitutions in any one of the CDR3 residues in the light chain and/or heavy chain sequence of any one of MAG-1, MAG-2, MAG-3, MAG-4, or MAG-5. In certain embodiments, the provasopressin-binding antibodies include antibodies having a single conserved amino acid substitution in any one of the CDR3 residues in the light chain and/or heavy chain sequence of any one of MAG-1, MAG-2, MAG-3, MAG-4, or MAG-5. In certain embodiments, the provasopressin-binding antibodies include antibodies having 2, 3, 4, or 5 conserved amino acid substitutions in any one of the CDR3 residues in the light chain and/or heavy chain sequence of any one of MAG-1, MAG-2, MAG-3, MAG-4, or MAG-5. Preferably, no more than one to five conservative amino acid substitutions are made within the VL and/or VH CDR3 domains. More preferably, no more than one to three conservative amino acid substitutions are made within the VL and/or VH CDR3 domains. Additionally, conservative amino acid substitutions (excluding Ala substitution) are not made at amino acid positions critical for antigen binding (e.g., those positions the substitution of which results in at least about 10-fold loss/increase in $K_d$ and/or $k_{off}$ values).

A "conservative amino acid substitution," as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). See Table A below for exemplary conservative substitutions.

The subject $AbnV_2$-binding antibodies may also include single chain (scFv) antibodies. The antibodies herein may be IgG antibodies, including IgG1, IgG2, IgG3, or IgG4 antibodies. In some embodiments, the antibody binds to an abnormal vasopressin $V_2$ receptor, such as $AbnV_2$, selectively.

The term "selective" or "selectively," as used herein in the context of selective binding, refers to a macromolecule (such as an antibody or antigen-binding portion thereof) that binds to its desired target ($AbnV_2$ or a fragment thereof) with a $K_d$ that is less than 2-fold, 5-fold, and preferably 10-, 20-, 50-, 100-, 200, 500-, or 1000-fold the $K_d$ of that antibody or antigen-binding portion thereof for any other wild-type human protein.

The term "abnormal vasopressin $V_2$ receptor ($AbnV_2$)-expressing tumor/cancer" as used herein refers to a tumor or a cancer that displays substantial expression of an abnormal vasopressin $V_2$ receptor, such as $AbnV_2$. The tumor/cancer may, for example, express at least 2, 5, 10, 20, 50, 100, 200, 500, or 1000-fold more abnormal vasopressin $V_2$ receptor ($AbnV_2$) than a corresponding wild-type tissue. The cancer may be malignant, and may be (locally) invasive and/or metastatic. The tumor may be benign.

A "therapeutically effective amount" refers to an effective amount of composition for causing a respective desired therapeutic effect, such as the tumor-/cancer-specific killing of tumor or cancer cells in a patient, eliminating one or more tumor/cancer cells, preventing said cells from proliferating, or inhibiting the rate of proliferation of said cells. Preferably, the therapeutically effective amount possesses a reasonable benefit/risk ratio applicable to the medical treatment.

By "treating" a patient suffering from tumor/cancer, it is meant that at least one of the patient's symptoms is partially or totally alleviated, remain static, or its progression retarded, following treatment according to the methods herein. A patient that has been treated can exhibit a partial or total alleviation of symptoms and/or tumor load, either temporarily or permanently. In certain embodiments, the term "treatment" may encompass prophylaxis use, therapy and cure. In certain embodiments, the term "treatment" may exclude prophylaxis use, therapy and cure.

3. Antibodies and Antigen-Binding Portions Thereof 3.1 Exemplary Abnormal Vasopressin $V_2$ Receptor-Binding Antibodies One aspect of the invention includes the various abnormal vasopressin $V_2$ receptor-binding agents, such as anti-$AbnV_2$ binding antibodies or antigen-binding portions thereof. Such binding agents, e.g., anti-$AbnV_2$ binding antibodies or antigen-binding portions thereof, may be produced using the abnormal vasopressin $V_2$ receptor ($AbnV_2$) described herein according to art recognized methods, including methods for producing antibodies, their antigen-binding portions thereof, and the various modified versions thereof with post-translational modifications. Such binding agents, e.g., anti-$AbnV_2$ binding antibodies or antigen-binding portions thereof, may be used in the methods of the invention described herein.

As used herein, "abnormal vasopressin $V_2$ receptor-binding antibody" include monoclonal or polyclonal antibodies. Such antibodies may be mouse antibodies, human antibodies, chimeric antibodies (such as human-mouse chimeric antibodies), or humanized antibodies. The antigen-binding portion thereof may include single chain scFv, Fab, F(ab')$_2$, Fd, Fv, dAb, bispecific antibodies, or other antibody fragments that retains all or substantially all binding affinity (e.g., no worse than 5, 10, 20, 50, 100, 200, 500 fold reduction, as measured by $K_d$ and/or $k_{off}$) of a full length antibody, such as an IgG1, IgG2, IgG3, or IgG4 antibody.

The antibody or its antigen-binding portion thereof may bind, preferably specifically, to any epitope on the exposed extracellular C-terminus of the abnormal vasopressin $V_2$ receptor, such as antibody or antigen-binding portion thereof that binds the peptide of SEQ ID NO: 1, or the most C-terminal six residues thereof. The antibody or antigen-binding portion thereof may also be specific for epitopes comprising post-translatinal modifications, including glycosylation.

In certain embodiments, the antibody may be in its native form. In certain embodiments, the antibody may be in forms containing a covalently or non-covalently conjugated moiety, such as an attached toxin, enzyme, fluorescent label, or radionuclide.

In some embodiments, the antibody or antigen-binding portion thereof comprises a purification tag. A purification tag may be used to facilitate purification of the antibody or antigen-binding portion thereof during the manufacturing process. Exemplary purification tag peptides include His, GST, TAP, FLAG, myc, HA, MBP, VSV-G, thioredoxin, V5, avidin, streptavidin, BCCP, Calmodulin, Nus, and S tags.

In certain embodiments, the abnormal vasopressin $V_2$ receptor-binding antibody is selective for abnormal vasopressin $V_2$ receptor. In other embodiments, the abnormal vasopressin $V_2$ receptor-binding antibody is selective for a particular epitope of the abnormal vasopressin $V_2$ receptor.

In certain embodiments, the subject antibody may also include antibody variants. Variants of any antibodies, or antigen-binding portions thereof, and peptides may have an amino acid sequence that is different by one or more amino acid substitutions from the amino acid sequence of a wild-type or original antibody. Embodiments which comprise amino acid deletions and/or additions are also contemplated. The variant may have conservative changes (amino acid similarity), wherein a substituted amino acid has similar structural or chemical properties, for example, the replacement of leucine with isoleucine. Guidance in determining which and how many amino acid residues may be substituted, inserted, or deleted without abolishing biological or proposed pharmacological activity may be reasonably inferred in view of this disclosure and may further be found using computer programs well known in the art, for example, DNASTAR® software.

Amino acid substitutions may be made, for instance, on the basis of similarity in polarity, charge, solubility, hydrophobicity, hydrophilicity, and/or the amphipathic nature of the residues as long as a biological and/or pharmacological activity of the native molecule is retained.

Negatively charged amino acids include aspartic acid and glutamic acid; positively charged amino acids include lysine and arginine; amino acids with uncharged polar head groups having similar hydrophilicity values include leucine, isoleucine, and valine; amino acids with aliphatic head groups include glycine, alanine; asparagine, glutamine, serine; and amino acids with aromatic side chains include tryptophan, phenylalanine, and tyrosine.

Example substitutions are set forth in Table A as follows:

TABLE A

| Original Residue | Example conservative substitutions |
| --- | --- |
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |
| Gly (G) | Ala; Pro |
| His (H) | Asn; Gln; Arg; Lys |
| Ile (I) | Leu; Val; Met; Ala; Phe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

3.2 Humanized Antibodies and Human Antibodies

One problem that antibody engineering attempts to address is the immune activity of a human patient that occurs in response to a native murine (or other non-human animal) antibody, typically a mAb, that is being administered to the patient for therapeutic purposes. This activity against murine antibodies is characterized by a human anti-mouse antibody (HAMA) response that can have deleterious effects on treatment efficacy and patient health. The HAMA response may be triggered when an antibody has epitopes recognized by human T cells. Thus, the antibodies described herein preferably are not recognized well by human T cells.

It has been found that almost all such human anti-non-human antibody ("HAMA type") activity is directed at the constant domains and at the FR regions of the variable domains of native non-human antibodies. Antibodies from other non-human animals have similar deleterious effects to a patient. The antibodies described herein may be humanized by any means known in the art.

By manipulating the nucleic acid molecules encoding antibody H and L chains, it is possible to incorporate non-human variable regions into antibodies otherwise made up of human constant regions. The resulting antibodies are referred to as "chimeric antibodies," and are typically less prone to eliciting HAMA type responses than are the non-human antibodies from which the variable regions are derived.

An alternative to eliminating the potential of a non-human antibody to elicit a HAMA type response is to "humanize" it, i.e., to replace its non-human framework regions with human ones. One way of achieving such humanization involves the insertion of polynucleotide fragments encoding the non-human CDRs of the antibody to be humanized into a nucleic acid molecule encoding an otherwise human antibody (with human constant regions if desired) so as to replace the human CDRs and to use the resulting nucleic acid molecule to express the encoded "humanized" antibody. If this process results in a loss of antibody-epitope affinity, selected humanized residues may be mutated back to their identity in the non-human antibody.

Detailed discussions of antibody engineering may be found in numerous publications including: Borrebaek, *Antibody Engineering, A Practical Guide*, 1992, W. H. Freeman and Co. NY; and Borrebaek, *Antibody Engineering*, 2nd ed. 1995, Oxford University Press, NY, Oxford (incorporated by reference).

A humanized antibody can be an antibody derived from a non-human species, in which certain amino acids in the framework and constant domains of the heavy and light chains have been mutated so as to reduce or abolish an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293 (incorporated by reference). A humanized antibody may comprise portions of immunoglobulins of different origin. For example, at least one portion can be of human origin. For example, the humanized antibody can comprise portions derived from an immunoglobulin of non-human origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Alternatively, a humanized antibody may be created in a transgenic or humanized animal expressing the human antibody genes (see Lonberg, N. "Transgenic Approaches to Human Monoclonal Antibodies," *Handbook of Experimental Pharmacology* (1994) 113: 49-101) (incorporated by reference).

Another example of a humanized immunoglobulin is an immunoglobulin containing one or more immunoglobulin chains comprising a CDR of non-human origin (e.g., one or more CDRs derived from an antibody of nonhuman origin) and a framework region derived from a light and/or heavy chain of human origin (e.g., CDR-grafted antibodies with or without framework changes). Chimeric or CDR-grafted single chain antibodies are also encompassed by the term humanized immunoglobulin.

One means of humanization is called COMPOSITE HUMAN ANTIBODY™ technology, which is described in detail in WO 2006/082406 (incorporated by reference). Briefly, the CDR regions are left intact or essentially intact. The non-human framework is replaced with a composite humanized framework. The composite humanized framework may be a chimera of several fragments from different endogenous human framework alleles. In this manner, a composite framework may be produced that resembles the antibody's non-human framework more closely than any given endogenous human framework.

In certain embodiments, the antibody of the invention may be fully human antibodies, such as isolated human antibodies. An entirely human antibody should, in theory, not elicit the HAMA reaction, even if used for prolonged periods. Fully human monoclonal autoantibodies may be prepared using human hybridoma techniques (see Boyle et al., *Cell. Immunol.* 152: 556-568, 1993; Boyle et al., *Cell. Immunol.* 152: 569-581, 1993; European Patent Application Publication No. 614 984 A2 by Boyle, et al.). Preferably, the human antibodies have a high affinity for its antigen, which affinity can be measured or calculate by conventional methods, such as $K_d$ or $k_{off}$ values that can be measured by surface plasmon resonance.

The term "surface plasmon resonance," as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 and Jonsson, U., et al. (1993) *Ann. Biol. Clin.* 51:19-26; Jonsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

Alternatively, the subject human antibodies may be produced by recombinant DNA technology using procedures well known in the art. Recombinant human antibodies preferably have high affinity (e.g., $K_d$ is about $10^{-7}$ M, $10^{-8}$ M, $10^{-9}$ M, $10^{-10}$ M or less) and a slow $k_{off}$ rate (e.g., $k_{off}$ is about $10^{-2}$ s$^{-1}$, $10^{-3}$ s$^{-1}$, $10^{-4}$ s$^{-1}$, $10^{-4}$ s$^{-1}$).

Methods of producing and selecting fully human antibody are well known in the art. See, for example, U.S. Pat. Nos. 4,800,155; 5,087,557; 5,196,337; 5,767,246; 6,090,383, 6,139,869; 6,787,153; 7,005,503 (all incorporated herein by reference).

3.3 Non-Antibody Binding Agents

Although the subject antagonists include antibodies, antigen-binding portions thereof, and variants thereof with amino acid sequence substitutions, the antagonists are not so limited. Other antagonists, including protein or nucleic acid based antagonists, may also be used in the subject methods.

In certain embodiments, the antagonist is an aptamer. Since the identification of the first RNA aptamer as an antagonist against bacterial phage T4 DNA polymerase in 1990, the SELEX (systematic evolution of ligands by exponential enrichment) process and its variations have been used successfully to identify aptamers for more than 100 diverse target molecules, including organic dyes, amino acids, biological cofactors, antibiotics, peptides, proteins, or even whole viruses (Bell et al., *J. Biol. Chem.* 273: 14309-14314, 1998; Gal et al., *Eur. J. Biochem.* 252: 553-562, 1998; Kraus et al., *J. Immunology* 160: 5209-5212, 1998; Yang et al., *Proc. Natl. Acad. Sci. U.S.A.* 95: 5462-5467, 1998; Eaton, *Curr. Opin. Chem. Biol.* 1: 10-16, 1997; Pan et al., *Proc. Natl. Acad. Sci. U.S.A.* 92: 11509-11513, 1995), showing that aptamers can be obtained for almost any desired target whether complex or small. See Famulok and Mayer, *Aptamers as Tools in Molecular Biology and Immunology,* In: *Combinatorial Chemistry in Biology. Current Topics in Microbiology and Immunology* (M. Famulok, C.-H. Wong, E.-L. Winnacker, Eds.), Springer Verlag, Heidelberg, 1999, 123-136 (all references incorporated by reference).

The SELEX process provides a powerful method for the screening of large libraries of oligonucleotides, with diversities of up to $10^{15}$ different molecules, for specific ligand-binding nucleic acids, which in many cases have been shown to not only bind a certain target protein, but also to inhibit its biological function. Such isolated aptamers routinely have high affinity and specificity for their respective targets, and are useful for various therapeutic and/or diagnostic applications. Furthermore, a wide spectrum of chemical modifications of nucleotides is known in the art, which can greatly increase the stability of RNA molecules in biological materials, thus considerably enhancing their application potential.

For example, any potential insufficient stability of the identified nucleic acids as therapeutic agents can easily be overcome by using libraries of chemically modified nucleic acids, such as 2'-fluoro- or 2'-amino-2'-deoxypyrimidine-containing nucleic acids. Such modifications have been shown to be compatible with the enzymatic steps of the SELEX process. Other strategies which circumvent the stability problem of RNA or DNA include the so-called mirror-image, or Spiegelmer, approach by exploiting nuclease resistance of the enantiomer of naturally occurring nucleic acids (KLUβMANN et al., *Nat. Biotechnol.* 14: 1112-1115, 1996; Nolte et al., *Nat. Biotechnol.* 14: 1116-1119, 1996).

The feasibility of using aptamers as an anti-AbnV$_2$ antagonist is evidenced by the existence of anti-vasopressin aptamers. Williams et al. successfully used the SELEX method (Williams et al., *Proc. Natl. Acad. Sci. U.S.A.* 94: 11285-11290, 1997, incorporated by reference) to identify L-ssDNA ligands to vasopressin. In their approach, D-DNA ligands have been selected using D-vasopressin as a target molecule. The enantiomer of the winning D-ssDNA aptamer, designated as L-ssDNA aptamer, has been synthesized and its ability to bind L-vasopressin was demonstrated. Importantly, this approach led to enhanced nuclease stability by mirror-image ssDNA (KLUβMANN et al., *Nat. Biotechnol.* 14: 1112-1115, 1996; Nolte et al., *Nat. Biotechnol.* 14: 1116-1119, 1996). The L-ssDNA-aptamer inhibited cAMP release mediated by vasopressin, but the cAMP release induced by oxytocin was not affected, demonstrating specificity in inhibitory biological activity.

Thus, in one aspect, the subject invention provides a method to identify aptamers that selectively bind abnormal vasopressin $V_2$ receptor or fragments thereof, the method comprising contacting a target protein, such as Abn$V_2$, with a library of candidate aptamers, and selectively identifying/isolating/enriching for aptamers that specifically bind the target protein. The identified aptamer may be similarly labeled by moieties including fluorescent dye, radioactive moiety, or a therapeutic agent, as described herein for antibody-based antagonists. Such labeled aptamers can be similarly used in the diagnostic and/or therapeutic applications of the invention, in a similar way the antibody-based antagonists are used.

In certain embodiments, the antagonist is a scaffold-derived binding protein specific for abnormal vasopressin $V_2$ receptor or any of its epitopes.

Engineering scaffold-derived binding proteins that are not members of the immunoglobulin family may possess novel binding functions resembling antibodies. Several classes of protein scaffolds have now been proven to yield reagents with specificities and affinities in a range that was previously considered unique to antibodies. See Skerra, *Current Opinion in Biotechnology,* 18(4): 295-304 (2007) (incorporated by reference). Such engineered protein scaffolds are usually obtained by designing a random library with mutagenesis focused at a loop region or at an otherwise permissible surface area, and by selection of variants against a given target via phage display or related techniques. Several classes of such engineered protein scaffolds have been demonstrated to yield specificities towards different kinds of targets, and to offer practical benefits such as robustness, smaller size, and ease of expression that justify their use as true alternatives to conventional antibodies or their recombinant fragments.

The most promising scaffolds with broader applicability include protein A, the lipocalins, a fibronectin domain, an ankyrin consensus repeat domain, and thioredoxin. Corresponding binding proteins are not only of interest as research reagents or for separation in biotechnology but also as potential biopharmaceuticals, especially in the areas of cancer, autoimmune and infectious diseases as well as for in vivo diagnostics.

Thus, in one aspect, the subject invention provides a method to identify scaffold-derived binding proteins that selectively bind abnormal vasopressin $V_2$ receptor or fragments thereof, the method comprising contacting a target protein, such as Abn$V_2$, with a library of candidate scaffold-derived binding proteins, and selectively identifying/isolating/enriching for scaffold-derived binding proteins that specifically bind the target protein. The identified scaffold-derived binding proteins may be similarly labeled by moieties including fluorescent dye, radioactive moiety, or a therapeutic agent, as described herein for antibody-based antagonists. Such labeled scaffold-derived binding proteins can be similarly used in the diagnostic and/or therapeutic applications of the invention, in a similar way the antibody-based antagonists are used.

In certain embodiments, the scaffold-derived binding proteins are derived from a scaffold of protein A, a lipocalin, a fibronectin domain, an ankyrin consensus repeat domain, or thioredoxin.

In certain embodiments, the antagonist is a fusion protein that functions similarly as an antibody. For example, the anti-Rheumatoid drug etanercept (trade name ENBREL®) treats autoimmune diseases by binding to tumor necrosis factor alpha (TNFα) as a TNFα inhibitor. It is a recombinantly expressed as a fusion protein between the human soluble TNF receptor 2 and the Fc component of human immunoglobulin G1 (IgG1). Such a fusion protein functions similarly as the human-mouse chimeric antibody against TNFα, such as infliximab (trade name REMICADE®).

Thus, any of the above protein based antagonists can be made as part of a fusion protein and be used in the methods of the invention. For example, a soluble moiety that specifically binds abnormal vasopressin $V_2$ receptor (such as a non-functional vasopressin) may be fused to the Fc region as in etanercept, and be used as an antagonist in the instant invention.

3.4 Linkers

It may be necessary in some instances to introduce an unstructured polypeptide linker region between a label and portions of the antagonist (e.g., antibodies or antigen binding portions). The linker can facilitate enhanced flexibility, and/or reduce steric hindrance between any two fragments. The linker can also facilitate the appropriate folding of each fragment to occur. The linker can be of natural origin, such as a sequence determined to exist in random coil between two domains of a protein. An exemplary linker sequence is the linker found between the C-terminal and N-terminal domains of the RNA polymerase a subunit. Other examples of naturally occurring linkers include linkers found in the lcI and LexA proteins.

Within the linker, the amino acid sequence may be varied based on the preferred characteristics of the linker as determined empirically or as revealed by modeling. For instance, in addition to a desired length, modeling studies may show that side groups of certain amino acids may interfere with the biological activity, e.g. DNA binding or transcriptional activation, of the protein. Considerations in choosing a linker include flexibility of the linker, charge of the linker, and presence of some amino acids of the linker in the naturally-occurring subunits. The linker can also be designed such that residues in the linker contact DNA, thereby influencing binding affinity or specificity, or to interact with other proteins. For example, a linker may contain an amino acid sequence which can be recognized by a protease so that the activity of the chimeric protein could be regulated by cleavage. In some cases, particularly when it is necessary to span a longer distance between subunits or when the domains must be held in a particular configuration, the linker may optionally contain an additional folded domain.

In some embodiments it is preferable that the design of a linker involve an arrangement of domains which requires the linker to span a relatively short distance, preferably less than about 10 Angstroms (Å). However, in certain embodiments, depending, e.g., upon the selected domains and the configuration, the linker may span a distance of up to about 50 Angstroms.

Antibodies described herein can be made recombinantly. Linkers may be added to the nucleic acid sequences of the heavy and light chains to increase flexibility of the antibody. In the case of a scFv, the linkers are added to connect the VH and VL chains and the varying composition can effect solubility, proteolytic stability, flexibility, and folding. In one embodiment, a linker of has the amino sequence GSTSG (SEQ ID NO: 2). In another embodiment, a linker has the amino sequence GGSSRSS (SEQ ID NO: 3). Linkers are well-known in the art and can comprise varied amino acid residues depending on the flexibility needed in the resulting recombinant protein to allow for biological activity.

3.5 AbnV$_2$ Nucleotide and Protein Sequences

In one aspect, the invention provides an abnormal vasopressin V$_2$ receptor (AbnV$_2$), which is encoded by an abnormal splicing variant of the mRNA for wt human vasopressin V$_2$ receptor. In certain embodiment, the abnormal vasopressin V$_2$ receptor (AbnV$_2$) is a tumor-specific truncated receptor that lacks the seventh trans-membrane region and has a unique extracellular C-terminal tail, such as the last six residues of SEQ ID NO: 1. In certain embodiment, the abnormal vasopressin V$_2$ receptor (AbnV$_2$) is capable of being internalized into a cell that expresses the abnormal vasopressin V$_2$ receptor (AbnV$_2$), such as a tumor/cancer cell.

A representative abnormal vasopressin V$_2$ receptor (AbnV$_2$) of the invention is a human protein represented by SEQ ID NO: 4, which comprises the last (most C-terminal) six residues of SEQ ID NO: 1 fused to the C-terminus of a truncated wildtype vasopressin receptor V$_2$ (UniProtKB/Swiss-Prot access No. P30518 (V2R_HUMAN)) ending at residues 302 and 303 (Leu-Glu).

The invention also includes variant AbnV$_2$ that is at least 85%, 90%, 95%, 96%, 97%, 98%, 99%, 99.3%, or 99.6% identical to SEQ ID NO: 4, preferably having the same six C-terminal residues of SEQ ID NO: 4.

The invention further includes a polynucleotide (DNA or RNA) encoding a protein sequence comprising the last 6 residues of an abnormal vasopressin V$_2$ receptor (AbnV$_2$) of the invention, such as the most C-terminal 6 residues of SEQ ID NO: 1.

The invention additionally includes a DNA or RNA probe capable of detecting the junction point where the most C-terminal 6 residues of SEQ ID NO: 1 is fused to residue 303 (Glu) of the wt human vasopressin receptor V$_2$. The junction point includes the intron-exon boundary between nucleotides 1271 and 1272 in SEQ ID NO: 5.

For example, the probe may be capable of hybridizing to a polynucleotide including or spanning the intron-exon boundary under high stringency hybridization (such as hybridizing in 6×SSC, 0.2% SDS, 1×Denhardt's blocking solution or 1% w/v milk, and 10-50 ng/mL denatured probe for 18-24 hrs; followed by washing at 65° C. in decreasing salt concentrations, such as 3×SSC/0.2% SDS, then 1×SSC/0.2% SDS, etc.), as is known in the art. See, e.g., Sambrook, Fritsch and Maniatis, *Molecular Cloning: A Laboratory Manual* (December, 1989).

In certain embodiments, the probe is capable of being used as a PCR probe, such as one used in an RT-PCT amplification using mRNA as template, and the resulting PCR product includes the intron-exon boundary. The PCR product may be about 50, 75, 100, 150, 200, 250, 300, 350, 400, 500, 600, 700, 800, 900, 1000 bp or more in length. One end of the PCR product may be 20, 30, 40, 50, 60, 70, 80, 90, 100, 150, 200, 250, 300, 350, 400, 450, or 500 bp from the intron-exon boundary.

In certain embodiments, the probe is no more than 40, 30, 25, 20, or 10 nucleotides in length, and is at least 5, 6, 7, 8, 9, or 10 nucleotides in length. Such probe may be included in a kit for detecting the presence or absence of the specific junction sequence nucleotides (e.g., mRNA from tumor/cancer samples), and the presence of absence of the nucleotide mutation (e.g., splicing mutation) that gives rise to the abnormal human vasopressin receptor V$_2$. Such kit may also contain other necessary components required for such detection, such as components required for PCR or RT-PCR reaction, fluorescent/radio label, etc.

A further aspect of the invention includes vectors comprising the AbnV$_2$ polynucleotide, fragments or complements thereof (such as expression vectors; gene therapy vectors encoding siRNA, microRNA, antisense sequence, or precursors thereof; adenoviral vectors, etc.), and a host cell that is introduced to contain such vectors.

4 Pharmaceutical Compositions

The antagonists (e.g., antibodies and antigen-binding portions) herein can be used, for example, for immuno-based targeting of tumors and delivery of chemotoxic/radiologic agents. Abnormal vasopressin V$_2$ receptor-expressing tumors can be localized and imaged using an antibody to the abnormal vasopressin V$_2$ receptor protein. Thus, antibodies, antigen-binding portions thereof, and their derivatives could be radiolabeled, conjugated to or used in conjunction with chemotoxic agents, or serve as an attractor for endogenous immune system cells to kill such tumors/cancers. Cancer vaccines may be based on tumor antigens, such as AbnV$_2$. Because of its unique expression in certain cancers, vaccine strategies based on AbnV$_2$, such as anti-antibodies or utilizing antigenic motifs on the AbnV$_2$ structure, could be developed that would enable the initial prevention and/or recurrence of these diseases.

4.1 Labels

The antagonists (e.g., antibodies and antigen-binding portions thereof) described herein may be labeled. As used herein, "label" is used to mean a detectable label which is used to visualize the binding of an antibody to its target protein or receptor. Alternatively, antibodies, antigen-binding portions thereof, and peptides may be labeled with, for example, a radiolabel, an iron-related compound, a fluorescent label, or a toxin which would kill or inhibit proliferation of the cell to which it binds. Radiolabels and toxins are well known in the art.

Non-limiting examples of radiolabels include, for example, $^{32}$P, $^{33}$P, $^{43}$K, $^{47}$Sc, $^{52}$Fe, $^{57}$Co, $^{64}$Cu, $^{67}$Ga, $^{67}$Cu, $^{68}$Ga, $^{71}$Ge, $^{75}$Br, $^{76}$Br, $^{77}$Br, $^{77}$As, $^{77}$Br, $^{81}$Rb/$^{81M}$Kr, $^{87M}$Sr, $^{90}$Y, $^{97}$Ru, $^{99}$Tc, $^{100}$Pd, $^{101}$Rh, $^{103}$Pb, $^{105}$Rh, $^{109}$Pd, $^{111}$Ag, $^{111}$In, $^{113}$In, $^{119}$Sb, $^{121}$Sn, $^{123}$I, $^{125}$I, $^{127}$Cs, $^{128}$Ba, $^{129}$Cs, $^{131}$I, $^{131}$Cs, $^{143}$Pr, $^{153}$Sm, $^{161}$Tb, $^{166}$Ho, $^{169}$Eu, $^{177}$Lu, $^{186}$Rc, $^{188}$Re, $^{189}$Re, $^{191}$Os, $^{193}$Pt, $^{194}$Ir, $^{197}$Hg, $^{199}$Au, $^{203}$Pb, $^{211}$At, $^{212}$Pb, $^{212}$Bi and $^{213}$Bi.

Non-limiting examples of toxins include, for example, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin.

Non-limiting examples of fluorescent labels include, for example, FITC, Texas Red, phycoerythrin (PE), cytochrome c, Cy3, and Cy5.

Non-limiting examples of metals such as iron-related compounds include, for example, magnetic iron-oxide particles, ferric or ferrous particles, $Fe_2O_3$, and $Fe_3O_4$. Iron-related compounds and methods of labeling antibodies and polypeptides can be found, for example, in U.S. Pat. Nos. 4,101,435 and 4,452,773, and U.S. published applications 20020064502 and 20020136693, all of which are hereby incorporated by reference in their entirety.

Additionally, other labels, such as biotin followed by streptavidin-alkaline phosphatase (AP), horseradish peroxidase (HRP) are contemplated.

Methodology for labeling proteins, such as antibodies, antigen binding portions thereof, and peptides are well known in the art. When the antibodies, antigen binding portions thereof, and peptides are labeled with a radiolabel or toxin, the antibodies, antigen binding portions thereof, and peptides can be prepared as pharmaceutical compositions which are useful for therapeutic treatment of patients exhibiting increased levels of abnormal vasopressin $V_2$ receptor wherein the pharmaceutical compositions are administered to the patient in an effective amount.

In some embodiments, the antibodies, antigen binding portions, or peptides are coupled to a polymer or a functionalized polymer (e.g., a polymer conjugated to another molecule). Examples include water soluble polymers, such as polyglutamic acid or polyaspartic acid, conjugated to a drug such as a chemotherapeutic or antiangiogenic agent, including, for example, paclitaxel or docetaxel.

In certain embodiments, particularly where the cytotoxic moiety is chemically cross-linked to the antibody, antigen binding portion, or peptide moieties, the linkage is hydrolysable, e.g., such as may be provided by use of an amide or ester group in the linking moiety.

In certain embodiments, the subject antibodies, antigen-binding portions thereof, or peptides can be coupled with an agent useful in imaging tumors. Such agents include: metals; metal chelators; lanthanides; lanthanide chelators; radiometals; radiometal chelators; positron-emitting nuclei; microbubbles (for ultrasound); liposomes; molecules microencapsulated in liposomes or nanosphere; monocrystalline iron oxide nanocompounds; magnetic resonance imaging contrast agents; light absorbing, reflecting and/or scattering agents; colloidal particles; fluorophores, such as near-infrared fluorophores. In many embodiments, such secondary functionality will be relatively large, e.g., at least 25 amu in size, and in many instances can be at least 50, 100 or 250 amu in size.

In certain preferred embodiments, the secondary functionality is a chelate moiety for chelating a metal, e.g., a chelator for a radiometal or paramagnetic ion. In preferred embodiments, it is a chelator for a radionuclide useful for radiotherapy or imaging procedures.

Radionuclides useful within the compositions and methods herein include gamma-emitters, positron-emitters, Auger electron-emitters, X-ray emitters and fluorescence-emitters, with beta- or alpha-emitters preferred for therapeutic use. Examples of radionuclides useful as toxins in radiation therapy include: $^{32}P$, $^{33}P$, $^{43}K$, $^{47}Sc$, $^{52}Fe$, $^{57}Co$, $^{64}Cu$, $^{67}Ga$, $^{67}Cu$, $^{68}Ge$, $^{71}Ge$, $^{75}Br$, $^{76}Br$, $^{77}Br$, $^{77}As$, $^{77}Br$, $^{81}Rb/^{81M}Kr$, $^{87M}Sr$, $^{90}Y$, $^{97}Ru$, $^{99}Tc$, $^{100}Pd$, $^{101}Rh$, $^{103}Pb$, $^{105}Rh$, $^{109}Pd$, $^{111}Ag$, $^{111}In$, $^{113}In$, $^{119}Sb$, $^{121}Sn$, $^{123}I$, $^{125}I$, $^{127}Cs$, $^{128}Ba$, $^{129}Cs$, $^{131}I$, $^{131}Cs$, $^{143}Pr$, $^{153}Sm$, $^{161}Tb$, $^{166}Ho$, $^{169}Eu$, $^{177}Lu$, $^{186}Re$, $^{188}Re$, $^{189}Re$, $^{191}Os$, $^{193}Pt$, $^{194}Ir$, $^{197}Hg$, $^{199}Au$, $^{203}Pb$, $^{211}At$, $^{212}Pb$, $^{212}Bi$ and $^{213}Bi$. Appropriate therapeutic radionuclides include $^{188}Re$, $^{186}Re$, $^{203}Pb$, $^{212}Pb$, $^{212}Bi$, $^{109}Pd$, $^{64}Cu$, $^{67}Cu$, $^{90}Y$, $^{125}I$, $^{131}I$, $^{77}Br$, $^{211}At$, $^{97}Ru$, $^{105}Rh$, $^{198}Au$ and $^{199}Ag$, $^{166}Ho$ or $^{177}Lu$. As used herein, "radionuclide" and "radiolabel" are interchangeable.

Conditions under which a chelator will coordinate a metal are described, for example, by Gansow et al., U.S. Pat. Nos. 4,831,175, 4,454,106 and 4,472,509 (incorporated by reference).

$^{99m}Tc$ is one appropriate radioisotope for diagnostic applications, as it is readily available to all nuclear medicine departments, is inexpensive, gives minimal patient radiation doses, and has good nuclear imaging properties. It has a half-life of six hours which means that rapid targeting of a technetium-labeled antibody is desirable. Accordingly, in certain preferred embodiments, the modified antibodies, antigen binding portions, and peptides include a chelating agent for technium.

In still other embodiments, the secondary functionality can be a radiosensitizing agent, e.g., a moiety that increases the sensitivity of cells to radiation. Examples of radiosensitizing agents include nitroimidazoles, metronidazole and misonidazole (see: DeVita, V. T. Jr. in *Harrison's Principles of Internal Medicine*, p. 68, McGraw-Hill Book Co., N.Y. 1983, which is incorporated herein by reference). The modified antibodies, antigen binding portions, and peptides that comprise a radiosensitizing agent as the active moiety are administered and localize at the target cell. Upon exposure of the individual to radiation, the radiosensitizing agent is "excited" and causes the death of the cell.

There are a wide range of moieties which can serve as chelators and which can be derivatized to the antibodies, antigen binding portions, and peptides described herein. For instance, the chelator can be a derivative of 1,4,7,10-tetraazacyclododecanetetraacetic acid (DOTA), ethylenediaminetetraacetic acid (EDTA), diethylenetriaminepentaacetic acid (DTPA) and 1-p-Isothiocyanato-benzyl-methyl-diethylenetriaminepentaacetic acid (ITC-MX). These chelators typically have groups on the side chain by which the chelator can be used for attachment to subject antibodies, antigen binding portions, and peptides. Such groups include, e.g., benzylisothiocyanate, by which the DOTA, DTPA or EDTA can be coupled to, e.g., an amine group.

In one embodiment, the chelate moiety is an "$N_xS_y$" chelate moiety. As defined herein, the term "$N_xS_y$ chelates" includes bifunctional chelators that are capable of coordinately binding a metal or radiometal and, preferably, have $N_2S_2$ or $N_3S$ cores. Exemplary $N_xS_y$ chelates are described, e.g., in Fritzberg et al. (1988) PNAS 85:4024-29; and Weber et al. (1990) *Bioconjugate Chem.* 1:431-37; and in the references cited therein.

The Jacobsen et al. PCT application WO 98/12156 provides methods and compositions, i.e., synthetic libraries of binding moieties, for identifying compounds which bind to a metal atom. The approach described in that publication can be used to identify binding moieties which can subsequently be added to antibodies, antigen binding portions, and peptides to derive the modified antibodies, antigen binding portions, and peptides described herein.

Certain of the subject labeled/modified antibodies, antigen binding portions thereof, and peptides can be synthesized, by standard methods known in the art, to provide reactive functional groups which can form acid-labile linkages with, e.g., a carbonyl group of the ligand. Examples of suitable acid-labile linkages include hydrazone and thiosemicarbazone functions. These are formed by reacting the oxidized carbohydrate with chelates bearing hydrazide, thiosemicarbazide, and thiocarbazide functions, respectively.

Alternatively, base-cleavable linkers, which have been used for the enhanced clearance of the radiolabel from the kidneys, can be used. See, for example, Weber et al. 1990 *Bioconjug. Chem.* 1:431. The coupling of a bifunctional chelate to antibodies, antigen binding portions, and peptides via a hydrazide linkage can incorporate base-sensitive ester moieties in a linker spacer arm. Such an ester-containing linker unit is exemplified by ethylene glycolbis(succinimidyl succinate), (EGS, available from Pierce Chemical Co., Rockford, Ill.), which has two terminal N-hydroxysuccinimide (NHS) ester derivatives of two 1,4-dibutyric acid units, each of which are linked to a single ethylene glycol moiety by two alkyl esters. One NHS ester may be replaced with a suitable amine-containing BFC (for example 2-aminobenzyl DTPA), while the other NHS ester is reacted with a limiting amount of hydrazine. The resulting hydrazide is used for coupling to the antibodies, antigen binding portions, and peptides, forming an ligand-BFC linkage containing two alkyl ester functions. Such a conjugate is stable at physiological pH, but readily cleaved at basic pH.

Antibodies and antigen binding portions thereof labeled by chelation can be subject to radiation-induced scission of the chelator and to loss of radioisotope by dissociation of the coordination complex. In some instances, metal dissociated from the complex can be re-complexed, providing more rapid clearance of non-specifically localized isotope and therefore less toxicity to non-target tissues. For example, chelator compounds such as EDTA or DTPA can be infused into patients to provide a pool of chelator to bind released radiometal and facilitate excretion of free radioisotope in the urine.

In still other embodiments, the antibodies and antigen binding portions are coupled to a Boron addend, such as a carborane. For example, carboranes can be prepared with carboxyl functions on pendant side chains, as is well known in the art. Attachment of such carboranes to an amine functionality, e.g., as may be provided on the antibodies, antigen binding portions, and peptides, can be achieved by activation of the carboxyl groups of the carboranes and condensation with the amine group to produce the conjugate. Such modified antibodies, antigen binding portions, and peptides can be used for neutron capture therapy.

The antibodies and antigen-binding portions thereof may also be modified with dyes, for example, useful in photodynamic therapy, and used in conjunction with appropriate non-ionizing radiation. The use of light and porphyrins is also contemplated and their use in cancer therapy has been reviewed by van den Bergh, *Chemistry in Britain,* 22: 430-437 (1986).

One embodiment includes antibodies and antigen binding portions thereof, labeled with a fluorescent label. Common fluorescent labels include, for example, FITC, PE, Texas Red, fluorescent nanodots, rhodamine, and the like. Techniques for labeling polypeptides and proteins are well-known in the art.

One embodiment includes antibodies and antigen binding portions thereof labeled with a metal compound, such as iron, which can be used in MRI imaging and/or for treatment. Iron-containing compounds include both ferrous and ferric-containing compounds, such as ferric-oxides. Specific examples include $Fe_2O_3$ and $Fe_3O_4$. Iron-containing compounds and methods of making iron-coupled antibodies and fragments thereof are described in U.S. Pat. Nos. 4,101,435 and 4,452,773 and published U.S. patent applications 2002/0064502 and 2002/0136693, all of which are hereby incorporated by reference in their entireties.

4.2 Chemotherapeutic Compounds

In certain embodiments, the antibodies and antigen binding portions thereof can be covalently or non-covalently coupled to a cytotoxin, chemotherapeutic agent, or other cell proliferation inhibiting compound, in order to localize delivery of that agent to a tumor cell. For instance, the agent can be selected from the group consisting of alkylating agents, enzyme inhibitors, proliferation inhibitors, lytic agents, DNA or RNA synthesis inhibitors, membrane permeability modifiers, DNA intercalators, metabolites, dichloroethylsulfide derivatives, protein production inhibitors, ribosome inhibitors, inducers of apoptosis, and neurotoxins.

Chemotherapeutics useful as active moieties which when conjugated to antibodies, antigen binding portions, and peptides are specifically delivered to tumorigenic cells are typically, small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication. Examples of known, useful cytotoxic agents are listed, for example, in Goodman et al., *The Pharmacological Basis of Therapeutics,* Sixth Edition, A. G. Gilman et al, eds./Macmillan Publishing Co. New York, 1980 (incorporated by reference). These include taxanes, such as paclitaxel (TAXOL®) and docetaxel (TAXOTERE®); nitrogen mustards, such as mechlorethamine, cyclophosphamide, melphalan, uracil mustard and chlorambucil; ethylenimine derivatives, such as thiotepa; alkyl sulfonates, such as busulfan; nitrosoureas, such as carmustine, lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, bleomycin, mithramycin and mitomycin; enzymes, such as L-asparaginase; platinum coordination complexes, such as cisplatin; substituted urea, such as hydroxyurea; methyl hydrazine derivatives, such as procarbazine; adrenocortical suppressants, such as mitotane; hormones and antagonists, such as adrenocortisteroids (prednisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone).

Drugs that interfere with intracellular protein synthesis can also be used; such drugs are known to those skilled in the art and include puromycin, cycloheximide, and ribonuclease.

Most of the chemotherapeutic agents currently in use in treating cancer possess functional groups that are amenable to chemical cross-linking directly with an amine or carboxyl group of an agent described herein. For example, free amino groups are available on methotrexate, doxorubicin, daunorubicin, cytosinarabinoside, bleomycin, gemcitabine, fludarabine, and cladribine while free carboxylic acid groups are available on methotrexate, melphalan, and chlorambucil. These functional groups, that is free amino and carboxylic acids, are targets for a variety of homobifunctional and heterobifunctional chemical cross-linking agents which can crosslink these drugs directly to a free amino group of an antibody, antigen binding portion thereof, or peptide.

Peptide and polypeptide toxins are also useful as active moieties, and the present disclosure specifically contemplates embodiments wherein the antibodies, antigen binding portions, and peptides are coupled to a toxin. In certain preferred embodiments, the antibodies, antigen binding portions, or peptides and the toxin are both polypeptides and are provided in the form of a fusion protein. Peptide and polypeptide toxins are generally complex toxic products of various organisms including bacteria, plants, etc. Examples of toxins include but are not limited to: ricin, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin.

Chemotherapeutic agents include chemotherapeutic drugs that are commercially available.

Merely to illustrate, the chemotherapeutic can be an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and/or a DNA repair inhibitor.

Chemotherapeutic agents may be categorized by their mechanism of action into, for example, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as *Cholera* toxin, ricin, *Pseudomonas* exotoxin, *Bordetella pertussis* adenylate cyclase toxin, or diphtheria toxin, and caspase activators; and chromatin disruptors. Preferred dosages of the chemotherapeutic agents are consistent with currently prescribed dosages.

4.3 Amino Acid Analogs

In certain embodiments, an antibody or antigen-binding portion thereof as described herein may comprise one or more amino acid analogs, derivatives and congeners of any specific amino acid referred to herein, as well as C-terminal or N-terminal protected amino acid derivatives (e.g. modified with an N-terminal or C-terminal protecting group). For example, one may use an amino acid analog wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and may be used according to the disclosures herein.

4.4 Combinations of Provasopressin Antibodies and Abnormal Vasopressin $V_2$ Receptor Antibodies In some embodiments, the antibodies and antigen-binding portions thereof may be co-administered with antibodies immunoreactive with provasopressin, preferably in a provasopressin-expressing (pro-VP-expressing) cancer, such as breast cancer, SCLC, neuroendocrine cancer (e.g., brain, gastroenteric, ovarian, endomedrial, testicular, adrenal, or skin cancer), prostate cancer, pancreatic cancer.

Thus, in certain embodiments, the subject antibodies or antigen-binding portions thereof may be used in conjunction with other antibodies specific for other antigens, such as the provasopressin-binding antibodies, including the monoclonal antibody produced by the hybridoma having ATCC Number PTA-5322, wherein the monoclonal antibody is MAG-1. Provasopressin-binding antibodies may also include the monoclonal antibody MAG-2, MAG-3, MAG-4, or MAG-5 (supra).

4.5 Pharmaceutical Additives

In certain embodiments, the antagonists (e.g., antibodies or antigen-binding portions thereof) are formulated with a pharmaceutically acceptable carrier. The antibodies or antibody variants can be administered alone or as a component of a pharmaceutical formulation (composition). They may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The subject formulations include those suitable for oral, dietary, topical, parenteral (e.g., intravenous, intraarterial, intramuscular, subcutaneous injection), inhalation (e.g., intrabronchial, intranasal or oral inhalation, intranasal drops), rectal, and/or intravaginal administration. Other suitable methods of administration can also include rechargeable or biodegradable devices and slow release devices such as slow release polymeric devices. The pharmaceutical compositions can also be administered as part of a combinatorial therapy with other agents (either in the same formulation or in a separate formulation).

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of anti-cancer therapeutic agent and a carrier and, optionally, one or more accessory ingredients. In general, the formulations can be prepared with a liquid carrier, or a finely divided solid carrier, or both, and then, if necessary, shaping the product.

Pharmaceutical compositions suitable for parenteral administration may comprise one or more antibodies, antigen-binding portions thereof, or peptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In some embodiments, the antibodies or antigen-binding portions are formulated with pharmaceutically acceptable carriers. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Injectable depot forms are made by forming microencapsule matrices of one or more antibodies in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, polymeric nanoparticles, or microemulsions which are compatible with body tissue.

In certain embodiments, the pharmaceutical composition is administered by subcutaneous, intravenous, intranasal, parenteral, transdermal, intracheal, intravenous, intramuscular, intracranial, intrathecal or intravitreal injection; by oral administration, eye drops, pessary, or inhalation.

To achieve the desired effects, the antibodies, antigen-binding portions thereof, or peptides can be administered in a variety of unit dosage forms. The dose will vary according to the particular antibody or antigen-binding portion thereof. For example, different antibodies may have different masses and/or affinities, and thus require different dosage levels. Antibodies prepared as Fab' fragments will also require differing dosages than the equivalent intact immunoglobulins, as they are of considerably smaller mass than intact immunoglobulins, and thus require lower dosages to reach the same molar levels in the patient's blood.

The dose will also vary depending on the manner of administration, the particular symptoms of the patient being treated, the overall health, condition, size, and age of the patient, and the judgment of the prescribing physician. Dosage levels of the antibodies for human subjects are generally between about 1 mg per kg and about 100 mg per kg per patient per treatment, and preferably between about 5 mg per kg and about 50 mg per kg per patient per treatment. In terms of plasma concentrations, the antibody concentrations are preferably in the range from about 5-1000 µg/mL, preferably 25 µg/mL to about 500 µg/mL.

Subject to the judgment of the physician, a typical therapeutic treatment includes a series of doses, which will usually be administered concurrently with the monitoring of clinical endpoints (such as tumor load or presence of abnormal vasopressin $V_2$ receptor fragments in the bloodstream) with the dosage levels adjusted as needed to achieve the desired clinical outcome. Other protocols can, of course, be used if desired as determined by the physician.

Administration of the compositions described herein may be performed by an intravascular route, e.g., via intravenous infusion by injection. Other routes of administration may be used if desired, such as s.c. injection. Formulations suitable for injection are found in *Remington's Pharmaceutical Sciences*, Mack Publishing Company, Philadelphia, Pa., 17th ed. (1985). Such formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, etc.

5 Diagnostic Methods

Applicants provide, inter alia, a rapid, inexpensive, sensitive, and specific method for: 1) early detection of cancer; and 2) identifying and localizing abnormal vasopressin $V_2$ receptor-expressing cancers, including metastatic and/or recurrent disease, in patients. Cancers that may be imaged using the methods herein include SCLC, breast cancer, and ovarian cancer.

In this respect it should be useful to all hospitals and physicians examining and treating patients with abnormal vasopressin $V_2$ receptor-expressing cancers. Detection kits are simple enough to be set up in any local hospital laboratory, and anti-abnormal vasopressin $V_2$ receptor (AbnV$_2$) antibodies and antigen-binding portions thereof can readily be made available to all hospitals treating patients with breast cancer.

5.1. Methods of Phenotyping Cancer Samples.

The instant disclosure also provides a method of phenotyping biological samples from patients having an abnormal vasopressin $V_2$ receptor-expressing cancer, such as SCLC, breast cancer, or ovarian cancer, comprising: (a) obtaining a biological sample from a patient; (b) (optionally) rendering the biological sample amenable to immunoassay; (c) contacting the rendered sample with the an antagonist of the abnormal vasopressin $V_2$ receptor, such as an abnormal vasopressin $V_2$ receptor-binding antibody or antigen-binding portion thereof, under conditions that allow for binding of the antagonist (e.g., antibody or antigen-binding portion) to the abnormal vasopressin $V_2$ receptor; and (d) determining if the cells of the rendered sample inappropriately express abnormal vasopressin $V_2$ receptor compared to a control tissue; wherein if the test tissue inappropriately expresses abnormal vasopressin $V_2$ receptor, the biological sample is identified as likely having cancerous cells.

In some embodiments, if the test tissue shows inappropriate expression, one may administer a therapeutically effective amount of an abnormal vasopressin $V_2$ receptor-binding antibody or antigen-binding portion thereof to the patient. In some embodiments, before step (a), the patient has been diagnosed as having an abnormal vasopressin $V_2$ receptor-expressing cancer, such as SCLC, breast cancer, or ovarian cancer.

5.2 Methods of Phenotyping Blood Samples for Non-Invasive or Less-Invasive Cancer Detection.

Certain tumors may be detected by measuring blood levels of abnormal vasopressin $V_2$ receptor components. This may be done with anti-abnormal vasopressin $V_2$ receptor antagonists (e.g., antibodies, antigen-binding portions thereof). These antibodies and antigen-binding portions thereof would be useful in the clinical screening assay to measure abnormal vasopressin $V_2$ receptor (or fragments thereof) levels in the blood of patients suspected of having abnormal vasopressin $V_2$ receptor-expressing tumors (such as breast cancer, ovarian cancer, or SCLC), or who have had those tumors in the past. This would be a useful, non-invasive or less invasive test to possibly justify further, more invasive tests/biopsies, and aid in monitoring recurrence of disease.

5.3 In Vivo Diagnostic Techniques

Herein Applicants disclose, among other things, a method of detecting a tumor in a patient having an abnormal vasopressin $V_2$ receptor-expressing cancer, such as SCLC, breast cancer, or ovarian cancer, comprising: (a) administering a pharmaceutical composition comprising an abnormal vasopressin $V_2$ receptor-binding antagonist (e.g., antibody or antigen-binding portion thereof) to the patient, (b) detecting the label, and (c) determining if the patient has cells that inappropriately express abnormal vasopressin $V_2$ receptor compared to a control; wherein if the patient has cells that inappropriately express abnormal vasopressin $V_2$ receptor, the patient is identified as likely having a tumor.

In certain embodiments, the method further comprises, if the patient has cells that inappropriately express abnormal vasopressin $V_2$ receptor, administering a therapeutically effective amount of an abnormal vasopressin $V_2$ receptor-binding antibody or antigen-binding portion thereof to the patient. In certain embodiments, before step (a), the patient has been diagnosed as having an abnormal vasopressin $V_2$ receptor-expressing cancer. The method may further comprise determining the location and/or volume of a plurality cells inappropriately expressing abnormal vasopressin $V_2$ receptor (for example, determining the volume of a tumor). This method may be used to determine the location of a tumor prior to surgical resection of the tumor. It may also be used to determine whether surgery is appropriate.

With the use of antagonists (e.g., antibodies) directed against various portions of the abnormal vasopressin $V_2$ receptor, current imaging techniques, such as MRI, could be greatly enhanced, and new imaging protocols for diseases such as SCLC, breast cancer or ovarian cancer could be developed and effectively implemented for clinical use. These types of techniques would be especially useful for the detection of metastatic disease. These techniques could also assist a surgeon preparing to surgically remove a tumor or tumors, by identifying the location of the tumor or tumors.

6. Therapeutic Methods 6.1 Methods of Therapy with Anti-Abnormal Vasopressin $V_2$ Receptor Antibodies Herein Applicants disclose, inter alia, a method of treating an abnormal vasopressin $V_2$ receptor-expressing cancer, comprising administering an effective amount of the pharmaceutical compositions described herein to a subject. These pharmaceutical compositions include anti-abnormal vasopressin $V_2$ receptor antagonists (e.g., antibodies, and antigen-binding portions thereof).

In certain embodiments, an antibody (or antigen-binding portion thereof) suitable for therapeutic use is a humanized antibody or antigen-binding portion thereof. The antibodies and antigen-binding portions may be humanized by any means known in the art, such as CDR grafting or generation of a chimeric antibody. Specific point mutations may also be made during the humanization process.

Antibodies can be used for targeting abnormal vasopressin $V_2$ receptor on certain tumors. It was shown previously that SCLC tumors can be localized and imaged in humans using radiolabeled antibody directed against the neurophysin portion of provasopressin. Subsequent studies show that polyclonal antibodies, monoclonal antibodies, and antibody Fab fragments directed against different regions of the provasopressin protein bind specifically to cultured SCLC and breast cancer cells, as well as to human tumor sections, but not to tissue that is devoid of tumor. Thus any antagonists specific for the abnormal vasopressin $V_2$ receptor is expected to perform similarly in a similar assay.

Described herein are polyclonal and monoclonal antibodies, and their Fab fragment derivatives, to abnormal vasopressin $V_2$ receptor, such as $AbnV_2$. It has been shown here that these antibodies and fragments can bind to cultured human cancer cells and human cancer tissue, such as those from SCLC and breast cancer. Since the abnormal vasopressin $V_2$ receptor is not typically found in normal cells, it can serve as an excellent target for tumor localization in the early detection, diagnosis, and treatment of cancers that express the abnormal vasopressin $V_2$ receptor. The subject abnormal vasopressin $V_2$ receptor also provides an attractive candidate for use in vaccine development strategies for the prevention of those cancers that express the gene.

Single-chain antibodies fragments and small binding peptides can be used for targeting abnormal vasopressin $V_2$ receptor on tumors. We also disclose single-chain variable region fragments (scFv) antibodies that bind to abnormal vasopressin $V_2$ receptor. The use of such smaller molecules will provide added benefits (tumor penetration, ease of manufacturing) for in vivo tumor targeting.

An effective therapeutic response is achieved when the patient experiences partial or total alleviation or reduction of signs or symptoms of illness, and specifically includes, without limitation, prolongation of survival.

In certain embodiments, a therapeutic response is achieved when the patient's symptoms remain static, and the tumor burden does not increase.

6.2 Methods of Combination Therapy

Herein Applicants disclose, inter alia, a method of treating abnormal vasopressin $V_2$ receptor-expressing cancers, comprising administering an effective amount of a pharmaceutical composition comprising an anti-abnormal vasopressin $V_2$ receptor antibody, or an antigen-binding portion thereof to a subject, and further comprising administration of a second treatment. The second treatment may be surgery, radiation therapy, or an effective amount of a second pharmaceutical composition, such as one or more anti-provasopressin antibodies including MAG-1, MAG-2, MAG-3, MAG-4, and MAG-5 (or any variants). The second pharmaceutical compositions may comprise a chemotherapeutic agent, and optionally comprising epinephrine. The pharmaceutical compositions may be administered concomitantly, in a single formulation, or in separate formulations. Alternatively, the second pharmaceutical composition may comprise one or more of dexamethasone, IBMX, and 8-bromoadenosine 3',5'-cyclic monophosphate (8br-cAMP). In one embodiment, the second pharmaceutical composition comprises each of dexamethasone, IBMX, and 8-bromoadenosine 3',5'-cyclic monophosphate (8br-cAMP). Alternatively, the second pharmaceutical composition may comprise one or more of IBMX and forskolin. In one embodiment, the second pharmaceutical composition comprises both of IBMX and forskolin.

Abnormal vasopressin $V_2$ receptor-binding antibodies and antigen binding portions can be used in combination therapy with chemotherapeutic agents. As described herein, abnormal vasopressin $V_2$ receptor-binding antibodies and antigen-binding portions thereof in combination with a cocktail of chemotherapeutic agents are effective at inhibiting proliferation of cancerous cells when administered in an effective amount.

For example, for small cell lung cancer (SCLC, including small cell carcinoma or oat cell cancer, and combined small cell carcinoma) treatment, other than surgery, radiation therapy, laser therapy, and endoscopic stent placement, the following chemotherapeutic agents may be used in combination therapy: Abitrexate (Methotrexate); Etopophos (Etoposide Phosphate); Etoposide; Etoposide Phosphate; Folex (Methotrexate); Folex PFS (Methotrexate); Hycamtin (Topotecan Hydrochloride); Methotrexate; Methotrexate LPF (Methotrexate); Mexate (Methotrexate); Mexate-AQ (Methotrexate); Toposar (Etoposide); Topotecan Hydrochloride; and VePesid (Etoposide).

For breast cancer treatment, other than surgery (including sentinel lymph node biopsy followed by surgery), and radiation therapy, the following chemotherapeutic agents or hormone therapy may be used in combination therapy: Abitrexate (Methotrexate); Abraxane (Paclitaxel Albumin-stabilized Nanoparticle Formulation); Adriamycin PFS (Doxorubicin Hydrochloride); Adriamycin RDF (Doxorubicin Hydrochloride); Adrucil (Fluorouracil); Afinitor (Everolimus); Anastrozole; Arimidex (Anastrozole); Aromasin (Exemestane); Capecitabine; Clafen (Cyclophosphamide); Cyclophosphamide; Cytoxan (Cyclophosphamide); Docetaxel; Doxorubicin Hydrochloride; Efudex (Fluorouracil); Ellence (Epirubicin Hydrochloride); Epirubicin Hydrochloride; Everolimus; Exemestane; Fareston (Toremifene); Faslodex (Fulvestrant); Femara (Letrozole); Fluoroplex (Fluorouracil); Fluorouracil; Folex (Methotrexate); Folex PFS (Methotrexate); Fulvestrant; Gemcitabine Hydrochloride; Gemzar (Gemcitabine Hydrochloride); Herceptin (Trastuzumab); Ixabepilone; Ixempra (Ixabepilone); Lapatinib Ditosylate; Letrozole; Methotrexate; Methotrexate LPF (Methotrexate); Mexate (Methotrexate); Mexate-AQ (Methotrexate); Neosar (Cyclophosphamide); Nolvadex (Tamoxifen Citrate); Novaldex (Tamoxifen Citrate); Paclitaxel; Paclitaxel Albumin-stabilized Nanoparticle Formulation Perjeta (Pertuzumab); Pertuzumab; Tamoxifen Citrate; Taxol (Paclitaxel); Taxotere (Docetaxel); Trastuzumab; Toremifene; Tykerb (Lapatinib Ditosylate); tamoxifen; Xeloda (Capecitabine); Aromatase inhibitor; PARP inhibitor; Doxorubicin Hydrochloride (Adriamycin) & Cyclophosphamide; Doxorubicin Hydrochloride (Adriamycin) & Cyclophosphamide & Paclitaxel (Taxol); Cyclophosphamide & Doxorubicin Hydrochloride (Adriamycin) & Fluorouracil; Cyclophosphamide & Methotrexate & Fluorouracil; Fluorouracil & Epirubicin Hydrochloride & Cyclophosphamide.

For ovarian cancer treatment, other than surgery, radiation therapy, immunotherapy, and vaccine therapy, the following chemotherapeutic agents given via i.v., i.p., or orally may be used in combination therapy: Adriamycin PFS (Doxorubicin Hydrochloride); Adriamycin RDF (Doxorubicin Hydrochloride); Carboplatin; Clafen (Cyclophosphamide); Cisplatin; Cyclophosphamide; Cytoxan (Cyclophosphamide); Doxorubicin Hydrochloride; Dox-SL (Doxorubicin Hydrochloride Liposome); DOXIL (Doxorubicin Hydrochloride Liposome); Doxorubicin Hydrochloride Liposome; Evacet (Doxorubicin Hydrochloride Liposome); Gemcitabine Hydrochloride; Gemzar (Gemcitabine Hydrochloride); Hycamtin (Topotecan Hydrochloride); LipoDox (Doxorubicin Hydrochloride Liposome); Neosar (Cyclophosphamide); Paclitaxel; Paraplat (Carboplatin); Paraplatin (Carboplatin); Platinol (Cisplatin); Platinol-AQ (Cisplatin); Taxol (Paclitaxel); Topotecan Hydrochloride; Bleomycin & Etoposide & Cisplatin (Platinol); Carboplatin & Paclitaxel (Taxol); Gemcitabine Hydrochloride & Cisplatin.

The above listed agents are merely for illustrative purpose only. One of ordinary skill in the art could prepare a formulation of any of the chemotherapeutic agents as described above to be administered with a preparation of one of the disclosed antibodies or antigen-binding portions thereof to treat an abnormal vasopressin $V_2$ receptor-expressing cancer.

7 Treatable Diseases

Using the methods described herein, one may treat a patient with an abnormal vasopressin $V_2$ receptor-expressing cancer. Examples of such cancers include SCLC, breast cancer (including invasive breast cancer or triple-negative breast cancer (estrogen receptor-negative, progesterone receptor-negative, and HER2-negative)), Ductal Carcinoma In Situ (DCIS), Atypical Ductal Hyperplasia (ADH), and ovarian cancer.

8 Kits

One embodiment includes for a kit useful for screening a biological sample for an abnormal vasopressin $V_2$ receptor-expressing cancer, and for identifying/selecting patients (form which the sample is derived from) for treatment, the kit comprising a preparation of an antagonist, such as an antibody or antigen binding portion immunoreactive with the abnormal vasopressin $V_2$ receptor or fragment thereof, wherein the antibody immunoreactive with the abnormal vasopressin $V_2$ receptor indicates the presence of an abnormal vasopressin $V_2$ receptor-expressing cancer. The kit may be labeled for use in detecting such tumors. The fragment of abnormal vasopressin $V_2$ receptor may be, for example, the exposed C-terminal domain lacking the $7^{th}$ transmembrane domain of the vasopressin $V_2$ receptor. If the biological sample is positive for abnormal vasopressin $V_2$ receptor, an abnormal vasopressin $V_2$ receptor-expressing cancer has been identified.

One embodiment of the kits include preparations of antibodies or antigen binding portions immunoreactive with abnormal vasopressin $V_2$ receptor or fragment thereof. Antibodies and antigen binding portions can be lyophilized or in solution. Additionally, the preparations can contain stabilizers to increase the shelf-life of the kits, e.g., bovine serum albumin (BSA). Wherein the antibodies and antigen binding portions are lyophilized, the kit can contain further preparations of solutions to reconstitute the preparations. Acceptable solutions are well known in the art, e.g., PBS.

Kits can further include the components for an ELISA assay for measuring abnormal vasopressin $V_2$ receptor and fragments thereof as tumor markers in body fluids. Samples to be tested in this application include, for example, plasma, urine, lymph, breast ductal secretions and products thereof. Alternatively, preparations of the kits may be used in immunoassays, such as immunohistochemistry to test patient tissue biopsy sections.

The compositions of the kit can be formulated in single or multiple units for either a single test or multiple tests. In certain embodiments, the preparations of the kit are free of pyrogens. The kits can include instructions for the use of the compositions in an immunoassay.

The practice of the present invention will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, *Molecular Cloning: A Laboratory Manual*, 3rd Ed., ed. by Sambrook and Russell (Cold Spring Harbor Laboratory Press: 2001); the treatise, *Methods In Enzymology* (Academic Press, Inc., N.Y.); *Using Antibodies*, Second Edition by Harlow and Lane, Cold Spring Harbor Press, New York, 1999; *Current Protocols in Cell Biology*, ed. by Bonifacino, Dasso, Lippincott-Schwartz, Harford, and Yamada, John Wiley and Sons, Inc., New York, 1999; *DNA Cloning*, Volumes I and II (D. N. Glover ed., 1985); *Oligonucleotide Synthesis* (M. J. Gait ed., 1984); Mullis et al. U.S. Pat. No: 4,683,195; *Nucleic Acid Hybridization* (B. D. Hames & S. J. Higgins eds. 1984); *Transcription and Translation* (B. D. Hames & S. J. Higgins eds. 1984); and *Current Protocols in Immunology, Molecular Biology, Cell Biology, Human Genetics, Protein Science, and Nucleic Acid Chemistry* (John Wiley & Sons, Inc., Edison, N.J.).

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

EXAMPLES

The present invention is illustrated by the following examples which should not be construed as limiting in any way. The contents of all cited references (including literature references, issued patents, published patent applications as cited throughout this application) are hereby expressly incorporated by reference.

Example I

Vasopressin $V_2$ Receptor Gene Expression and the Nature of $AbnV_2$

Using RT-PCR and sequencing with nested primers, Applicants were able to show that the gene for vasopressin $V_2$ receptor is expressed for all four SCLC cancer cell lines (NCI H82, NCI H345, NCI H146, DMS-53) examined.

It has been shown that SCLC cancer cells, particularly recurrent SCLC cancer cells, express an abnormal mRNA message for the $V_2$ receptor. The abnormal mRNA apparently arises from alternative slicing, and contains the entire 106 bases of the intron 2 sequence of the $V_2$ receptor gene. Such an abnormal mRNA, through reading of a premature stop codon, gives rise to a truncated $V_2$ receptor ($AbnV_2$) lacking the seventh trans-membrane domain. As a result, the specific C-terminal structure is outside the plasma membrane, and is available for targeting (e.g., by antibodies).

Applicants generated antibodies against the abnormal C-terminal sequence of this receptor using the procedure below.

Specifically, the peptide antigen for the generation of the Abner monoclonal antibody was $NH_2$-YLEGGCSRG-OH ($NH_2$-Tyr-Leu-Glu-Gly-Gly-Cys-Ser-Arg-Gly-OH, SEQ ID NO: 1). This represents the unique hexapeptide C-terminus of the abnormal $V_2$ receptor (the last six residues of SEQ ID NO: 1) attached at the N-terminus to two residues (Leu-Glu) that the abnormal $V_2$ receptor shares with the normal $V_2$ receptor, and an N-terminal tyrosine (Tyr or Y) added to allow a radioactive iodide to be added for binding tests. Thus one aspect of the invention also relates to this peptide antigen used to generate Abner-like monoclonal antibodies.

To produce an antigen for immunization, the above peptide was mixed in saline with bovine thyroglobulin at a molar ratio of 100 (peptide): 1 (bovine thyroglobulin). The peptide was then coupled to bovine thyroglobulin with glutaraldehyde at 10 times the molar concentration of the peptide. Complex formation was allowed to proceed with stirring at ambient temperature for about 4 hours, and the resulting product was dialysed (exclusion 10 kDa) with 3×1,000 mL distilled water. The retained fraction was made 1 mg/mL (peptide equivalents) with saline and sonicated 1:1 with complete Fruend's adjuvant. This final solution was injected subcutaneously at multiple sites along the back of BALBC mice. Following a post-immunization period of 4 weeks, a sonicated mixture of the complex at 1 mg/mL (peptide equivalents) in saline was sonicated with an equal volume of incomplete Fruend's adjuvant, and the resulting product was used to boost immunize. Following another period of 3 weeks, a second boost injection was given, and the spleen of the immunized mice was removed after another 10 days. A preparation of white cells from the removed spleen was mixed 5:3 with SP2/0 mouse myeloma cells and these hybrided using PEG. Hydridomas were prepared through dilution cloning. The resulting clones were screened for monoclonal antibody. One of the produced monoclonal antibodies was named Abner1, and has a dissociation constant for its antigen of about $6.4 \times 10^{-8}$ M. Unless specifically indicated otherwise, this antibody was used in the experiments below where a mouse monoclonal Abner antibody was used.

Using the Abner1 monoclonal antibody so generated, Applicants showed via Western Analysis that a protein representing the truncated $AbnV_2$ receptor was present in the NCI H82 and three other (primary disease-derived) SCLC cell lines examined. These results demonstrate that the abnormal $AbnV_2$ receptor is expressed at the surface of tumor cells, including NCI H82 (see below).

Example II $AbnV_2$ Expression in SCLC

Immunohistochemistry (IHC) was performed on SCLC cancer sections from 22 patients, including 8 with recurrent disease (see FIG. 1).

The polyclonal Antibodies employed in these studies were generated against the unique and extracellular C-terminal domain of the $AbnV_2$ receptor. To generate the antibody, an amidated peptide was coupled to bovine thyroglobulin as an effective antigen for generating polyclonal antibodies in rabbits.

For IHC, the active IgG2b fraction of the antiserum was isolated using protein A Sepharose. The sABC technique of IHC, with citrate "antigen recovery," on 4 µm sections was employed (SSI System, Biogenex). As a control, excess peptide antigen was used to block the primary antibody.

These studies revealed the presence of $AbnV_2$ in seemingly all neoplastic cells of all tumor tissue sections examined. Meanwhile, no staining was found in normal kidney, breast, liver, and lung tissue sections.

Example III $AbnV_2$ Receptor is Present on Cell Surface

Figure 2A:
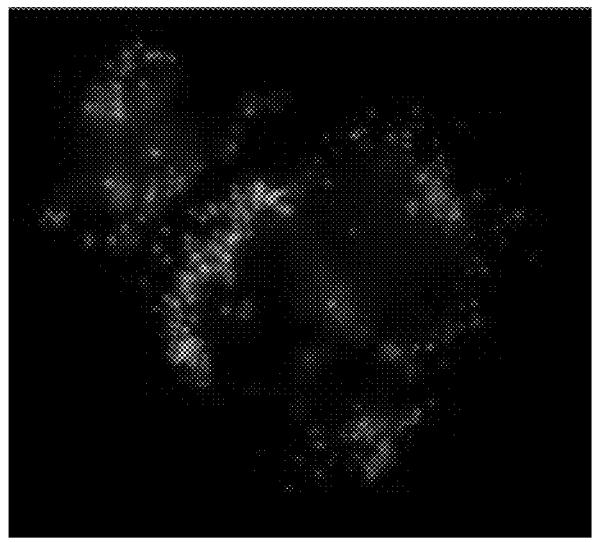
FIGS. 2A and 2B show surface fluorescent staining of AbnV$_2$ receptor on NCI H82 cells. AbnV$_2$ staining is in colored dots on the left (FIG. 2A), while nuclear staining with DAPI is a large nucleus-shaped staining on the right (FIG. 2B).
Figure 2B:
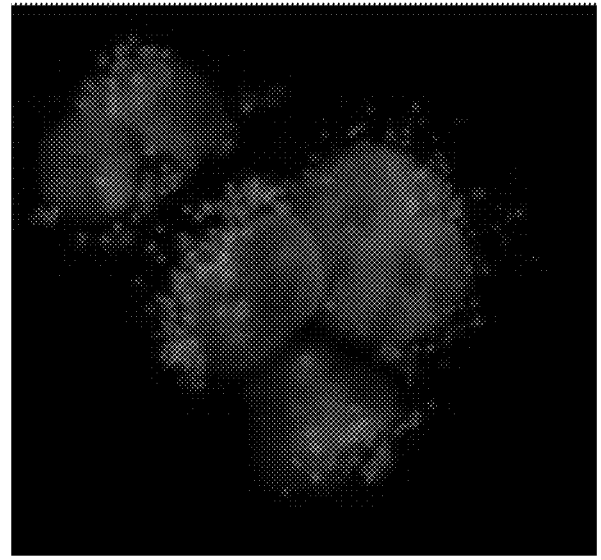

Applicants have previously demonstrated via Western Analysis that the $AbnV_2$ receptor is present in the NCI H82 and NCI 345 cell lines. Applicants have further confirmed that the abnormal receptor is present on cell surface via confocal microscopy employing a monoclonal antibody specific for a unique extracellular C-terminal fragment of $AbnV_2$. See above and FIGS. 2A and 2B, which show surface fluorescent staining of the abnormal $AbnV_2$ receptor on NCI H82 cells. This suggests that antagonists raised against the extracellular C-terminal fragment of $AbnV_2$ will be able to target the that portion of the abnormal receptor for diagnosis and/or treatment.

Example IV

Anti-$AbnV_2$ Antibody Impairs Tumor Growth In Vitro

This experiment demonstrates that anti-$AbnV_2$ mouse polyclonal antibody decreases the viability of NCI H82 cancer cells, which represents recurrent SCLC.

NCI H82 cancer cells were plated in 96-well plates at $1$-$2 \times 10^4$ cells/well. The cells were incubated with PBS/glycine containing albumin (1.25 mg/mL), in the presence of different amounts of anti-$AbnV_2$ polyclonal antibody preparation at indicated dilutions, or vehicle. Alamar Blue was later added to each well following an incubation period. Fluorescent readings were taken at excitation 530-560 nm and emission 590 nm and above, on a SYNERGY HT Multi Detection Reader.

Figure 3:
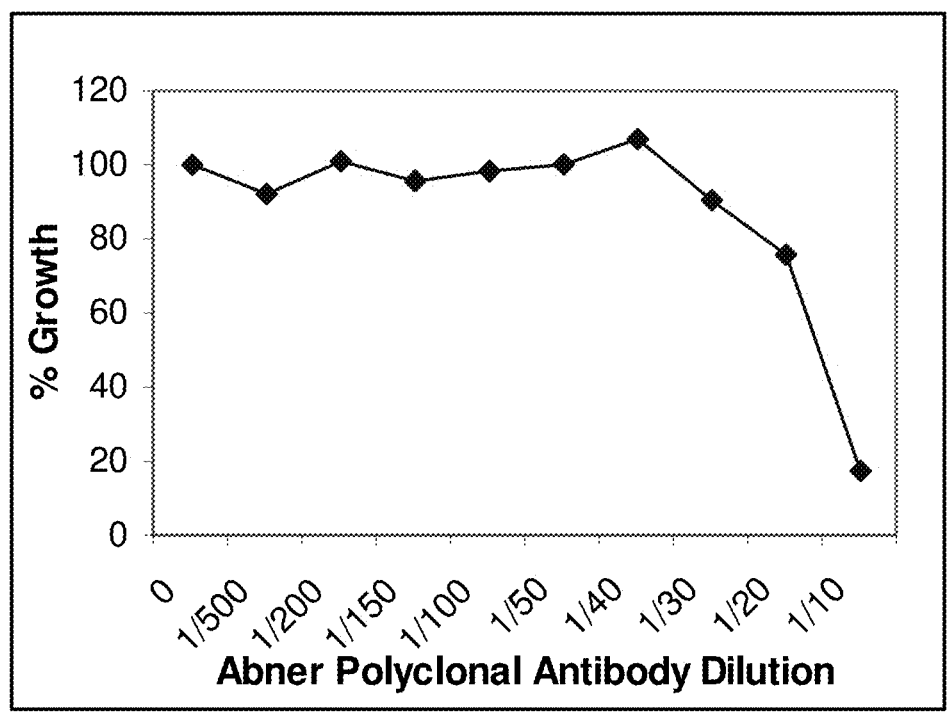
FIG. 3 shows influence of anti-AbnV$_2$ antibody on NCI H82 SCLC cancer cell proliferation. Reduction in fluorescence as % growth reflects reduction in cell viability following incubation with different dilutions of antibody over 24 hours.

As shown in FIG. 3, the anti-$AbnV_2$ polyclonal antibody produced dramatic reductions in cell viability and cell proliferation in the NCI H82 recurring SCLC cells.

Example V

Treatment of SCLC Tumor Xenografts

This experiment demonstrates that SCLC tumor xenografts can be treated (e.g., growth inhibited) by native (unmodified) anti-GRSA monoclonal antibody.

GRSA is a cell surface antigen that relates to vasopressin expression. Small-cell lung cancer NCI H345 cells were grown as xenografts in nu/nu mice, which were treated with an unmodified form of an IgG1 mouse monoclonal antibody raised against the C-terminus of GRSA.

In the first study, Applicants compared treatment with 50 µg/25 gm b.w. anti-GRSA administered i.p., on alternating days for 6 days (day 0, 2, 4, 6), with no treatment as the control. In a later study, 100 µg/25 gm b.w. (body weight) of these antibodies was administered i.p. daily for 15 days. Tumor growth was measured daily for 10-20 days beyond the final treatment.

Figure 4A:
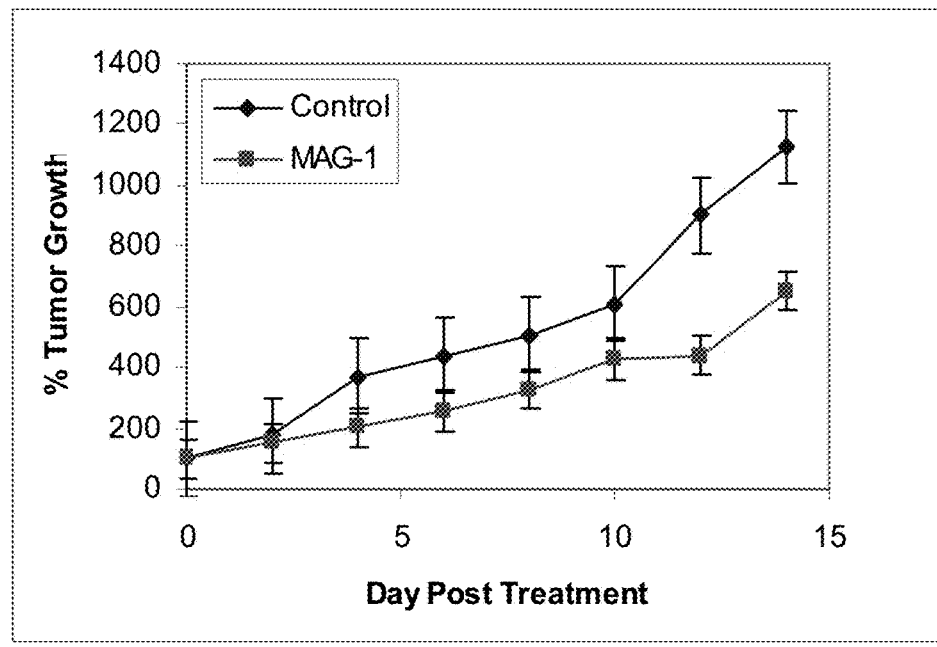
FIGS. 4A and 4B show the effect of anti-GRSA antibody on SCLC growth.
Figure 4B:
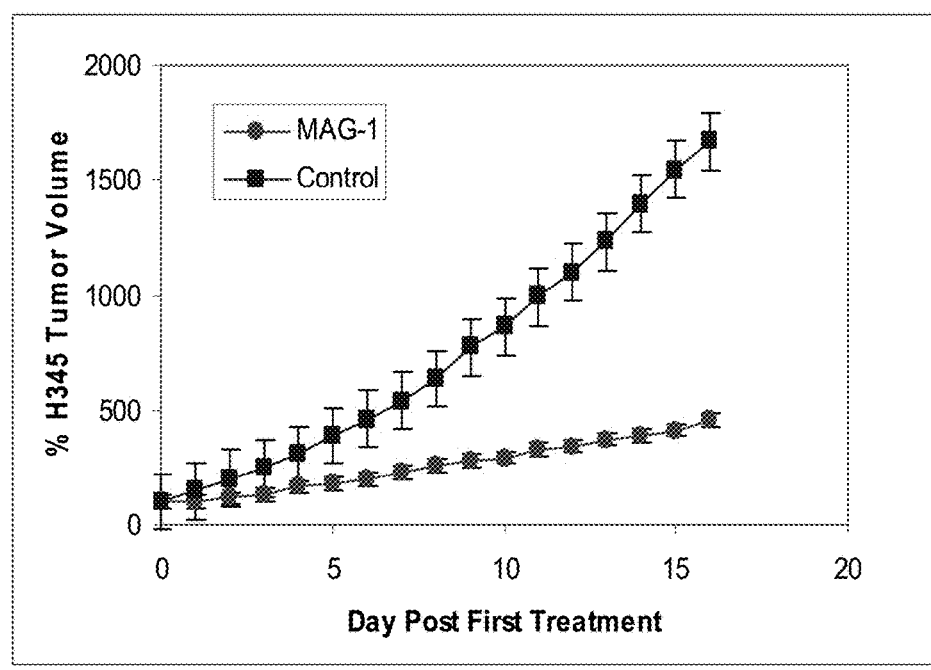

Four animals were used in each group. Body weight was measured daily. At the end of the study, tumor, liver, and kidneys were examined for possible pathological changes. The results are shown in FIGS. 4A & 4B.

In all cases, anti-GRSA treatments caused a significant reduction in the rate of tumor growth. The effect seemed to be dose-dependent. The lower dose produced a reduction to about 50% of control growth rate, while the higher dose reduced growth rate to about 33% of that shown by untreated tumors.

MOPC21-treated tumors showed rapid growth, such that at 16 days, they were about 4.5 times the size compared to that at the start of the study. In fact, these tumors became so large (most >8000 mm$^3$) that control animals had to be terminated at day 16. Histological evaluation of normal tissues revealed no damage by extensive treatment with anti-GRSA. In contrast, treated tumors contained massive internal apoptosis, such that the tumor cells became fluid-filled (data not shown). The result demonstrates the feasibility of using native anti-$AbnV_2$ antibody to treat SCLC tumors.

Example VI

Treating NCI H82 Xenograph Tumors in Mice by Anti-AbnV$_2$ mAb

This experiment shows that anti-AbnV$_2$ monoclonal antibody directed against the C-terminus of AbnV$_2$ receptors, or $^{90}$Yttrium-labeled forms thereof, can be used in therapy.

Dosing and treatment schedules are based on previous experiments in mice with monoclonal antibody to another SCLC marker pro-VP. The results are expected to show that unmodified AbnV$_2$ monoclonal antibody and/or $^{90}$Yttrium-labeled monoclonal antibody can destroy NCI H82 cancer tumor xenografts, cause considerable reduction in tumor size, or retard tumor growth, in nu/nu mice.

NCI H82 SCLC cells are grown as subcutaneous tumor xenografts for 14-21 days (to reach a tumor diameter of about 0.5 to 0.75 cm) in nu/nu mice. Two studies are conducted with this cell line, one involving treatment with native (unmodified) antibody, the second with $^{90}$Yttrium-labeled antibody.

Three days before tumor treatments commences, animals with sizeable xenografts are randomized into three groups (N=8 per group), and tumor sizes are measured daily.

In the first study, on Day 0 of treatment, and for the next 20 days, the control group 1 only receives daily i.p. injections of PBS vehicle. Two other groups receive daily i.p. doses, each comprising 150 μg/25 gm body weight (6 mg/kg body weight, based on similar amounts to mice used in initial Herceptin studies) of a ubiquitous IgG (e.g., MOPC21) as control, or anti-AbnV$_2$ monoclonal antibody for 20 days.

For the second study, two groups receive 50 μCi/25 gm body weight of $^{90}$Y-labeled MOPC21 (~2 μg) with 148 μg/25 gm body weight unmodified MOPC25, or the same amount of $^{90}$Y-anti-AbnV$_2$ and unmodified anti-AbnV$_2$. Tumor size is measured in blinded fashion at daily intervals, for 30 days following commencement of treatment. Body weight is measured daily for at least 30 days to evaluate toxicity. At the end of the study, brain, liver, kidney, and spinal chord are fixed, blocked, sectioned, and stained, for a review of organ toxicity by a pathologist.

Applicants have observed that, at 2-3 weeks after tumor cell implantation, SCLC tumors reach a size of about 1 cm in diameter, and begin to grow at a rate doubling their size every 4-7 days. A total of 48 animals (2×24) are used for the two studies.

This study focuses on comparing the tumor growth rates for the 3 groups of mice. For each mouse, longitudinal data on the tumor size (in mm$^3$) is collected. The theory of re-growth curves [24, 25] is applied to quantify tumor re-growth and treatment effect in each group. This theory has been successfully applied and published in a series of publications with a similar tumor growth delay data analysis [see 26, 27 for references].

Three cancer treatment endpoints will be used: doubling time, tumor growth delay, and cancer cell surviving fraction in vivo. The re-growth curves are estimated using the theory of mixed models with longitudinal tumor volume data. As was shown in previous studies, this technique adequately reflects the notorious variation of animal response to treatment through the presence of random effects. Two types of re-growth curves are applied: double exponential curve [24] and LINEXP [25]. A total of 24 mice are used for each experiment (3 groups with 8 mice per group).

Although 100 μg/25 gm body weight/day of anti-GRSA monoclonal antibody was sufficient to reduce growth of primary SCLC by two-thirds, more than 150 μg/day of antiAbnV$_2$ may be required to produce the same or greater effects with recurrent SCLC. To allow for this possibility, pilot studies are conducted with a few mice and a range from 150-300 μg to determine the ideal concentration for anti-AbnV$_2$. An effect is expected with the native antibody, partly because of the effects seen with NCI H82 growth in vitro.

It is possible, but not likely that higher amounts of radioactivity might be required, because similar levels/dosages have been used effectively before [28] as an amount that influences tumor growth without serious side-effects.

Example VII

AbnV$_2$ as a Tumor-Specific Disease Marker

The study evaluates the incidence and abundance of AbnV$_2$, for recurrent and primary SCLC tumors, and for a range of normal human tissues, by IHC using a modified ABC procedure, and by RIA.

The available monoclonal antibody against the unique C-terminal region of the AbnV$_2$ is used for the IHC studies and RIA. Positive staining (+3 and +4) for AbnV$_2$ has already been shown in SCLC for all twenty-two patients examined from an archival library, including 8 with recurrent disease, and all four SCLC cell lines in culture, including NCI H82, either by IHC, RT-PCR, Western analysis, or by con-focal microscopy.

The chief source of SCLC tumors, and 33 normal human tissues to be examined are on commercially available microarrays. An extensive archival library of fixed SCLC tissues can also be accessed through a Pathology archive. Blocks of these tissues include both formalin and AMEX fixed preparations.

Antibodies against AbnV$_2$ are tested against arrays of normal tissues to ensure specificity and/or sufficient selectability. Monoclonal antibodies generated from hybridoma cells, and purified by protein A and G chromatography are used in this study. For IHC, the sABC technique, with or without "antigen recovery," on 4 μm sections is employed (SSI System, Biogenex). Additional sections of 10 μm are extracted for receptor proteins/peptides [32], and extracts are assayed using established methods of RIA [33* 34* 35*] and ELISA.

It has been previously shown that the antibodies do not react with normal human breast, lung, kidney, and liver tissues under the conditions used for staining. For RIA, weighed (and heated for antigen retrieval if formaldehyde-fixed) tissue sections are investigated for obtaining quantitation with RIA and ELISA for AbnV$_2$, so the levels of this receptor protein are related post hoc to prognosis.

Both polyclonal and monoclonal antibodies are available for the study. A very sensitive RIA and ELISA for AbnV$_2$ have recently been developed, which can be used to quantitate the receptor in tissues.

Statistical analysis for this study focuses on estimating the rate of AbnV$_2$ receptor protein presence in the group of tumors studied, particularly recurrent tumors. The rate of receptor presence is estimated as a ratio of the number of tumors positive for each receptor to the total number of tumors studied. A 95% confidence interval is constructed using exact binomial.

It is expected that the actual rate of marker positivity is over 90 percent, based on observations obtained from tumor materials from 120 patients. From each patient, it will be determined whether the marker is present or absent. Based on an exact test, it is expected that the rate of tumor marker positivity is over 90 percent if the marker is present in 114 or more samples. The probability of making this conclusion when the actual rate of marker positivity is 90 percent or less is at most 0.038.

Example VIII

Mechanism for Anti-AbnV$_2$ Antibody Inhibition of Tumor Cell Growth and Survival The experiments described herein are designed to examine the influence that the subject anti-AbnV$_2$ antibodies have on key growth promoting signal transduction pathways, the levels of free-intracellular calcium, cell viability, and the expression of key proteins involved in cell growth, cell cycle, drug resistance, tumor suppression, and tumor death. NCI H82 and NCI H345 cells are incubated with an anti-AbnV$_2$ antibody for times ranging from 30 sec to 72 hours at 37° C.

Cytotoxicity and Apoptosis Assay: APOTOX-GLO™ Triplex Assay (and any one component of this triple assay) and Tunel assay [36] are used to determine cytotoxicity and apoptosis induced in NCI H82 and NCI H345 small-cell lung cancer cells by anti-Abn$V_2$ antibody. Employment of the Stress & Toxicity PathwayFinder PCR Array and the Apoptosis PCR Array (SABiosciences) are expected to provide information concerning which 84 genes of stress and cytotoxicity, and which 84 genes of apoptosis, are affected by the antibody. Optionally, Western analysis is used to follow-up specific proteins identified in the anti-Abn$V_2$ trigger cytotoxic and apoptotic pathways.

Selective Knockdown of Abn$V_2$: Using manufacturer's methods, shRNA Lentiviral (Santa Cruz) is employed to develop, and select out with puromycin (2 μg/mL), Vasopressin $V_2$ receptor gene knockdown stable transforms of NCI-H82 and NCI H345 cells, with knockdown confirmed by real-time RT-PCR and Western Blotting. The influence knockdown has on anti-Abn$V_2$ monoclonal antibody influence on cell growth is assessed with Alamar Blue, by comparing their effects with those in cells modified with lentiviral particle control. The influence of anti-Abn$V_2$ antibody on the growth of tumors derived from these selected cell lines is also determined (see below).

Western Analysis of Pathways affected by anti-Abn$V_2$ Antibody: Adhered cells are serum starved for 12 hr prior to treatment with 1-50 μg/mL anti-Abn$V_2$ monoclonal Antibody or vehicle, for 1 h, 2 h, 4 h, 24 h, and 48 h. Cells are lysed in RIPA buffer, pH 7.4 and centrifuged at 10,000×g for 4 min at ambient temperature. Supernatents are then mixed with 3×Laemmli sample buffer containing 3% mercaptoethanol, and heated for 5 min at 100° C. Protein extracts are subjected to 10% SDS PAGE, and transferred to PVDF membranes. Blocked membranes are probed at 4° C. with antibodies to recognized pathway proteins such as anti-phospho-ERK1/2, anti-ERK1/2, and anti-phospho-MEK (Cell Signal Technologies), and visualized following treatment by secondary Ab-HRP complex, and ECL reagents. For quantification, membranes are scanned and analyzed with Quantity One 4.2.1 software (BioRad).

SemiQuantitative RT-PCR and Quantitative RT-PCR: Total RNA is extracted from cells following treatment using TRIzol (GibcoBRL), and is then reverse transcribed (Invitrogen) to produce cDNA, for amplification by PCR for specific growth-related products (Superarray Technologies). For quantitative analysis, transcription analysis kits (such as that from Superarray Technologies), in addition to the Stress & Toxicity Pathfinder PCR Array and the Apoptosis PCR Array of SABiosciences, may be used for evaluating transcription pathways, growth factors, and drug resistance with Real-Time PCR, on an available ICYCLER of BioRad, and quantitation with SYBR Green.

Ability of Monoclonal Antibody to Kill Abn$V_2$ Knockdown Tumors in Mice: With established techniques, the effect of puromycin-triggered shRNA knockdown of Abn$V_2$ on reducing the growth rates of growing breNCI H82 tumors is determined. Also determined is the effect of unmodified monoclonal antibody on reducing tumor xenografts in nude mice, which have had Abn$V_2$ marker considerably reduced by shRNA gene knockdown.

ADCC Assay: Antibody-dependent cell-mediated cytotoxicity (ADCC) of anti-Abn$V_2$ on NCI H82 cells is performed based on $^{51}$Cr release as described [37]. Briefly, NCI H82 (target) cells are harvested at about 30-60% confluency, and are labeled with $^{51}$Cr at about 100 μCi per $5\times10^5$ cells for 2 hrs. After labeling, the cells are washed extensively before use. Buffy coat cells, as effector cells, are isolated from healthy volunteers by centrifugation at 650 g for 10 minutes. The buffy coat cell counts are determined after lysing the red blood cells in 2% acetic acid. To each well of a 96-well plate, $5\times10^3$ $^{51}$Cr-labeled H345 cells in 50 μL are added. Then, $7\times10^5$ buffy coat cells in 100 μl are added to the well, with an effector-to-target ratio of about 140:1. Subsequently, about 1 μg of anti-Abn$V_2$, or MOPC21 (negative control) in 50 μL is added to the well, to a final volume of about 200 μL. The plate is incubated at 37° C. for about 4 hrs. After centrifugation, $^{51}$Cr release (as measured in cpm) in triplicates is determined. The percentage of cellular cytotoxicity is calculated using the formula below:

$$\%\ \text{Specific lysis}=(\text{Sample Count}-\text{Spontaneous Release})/(\text{Total Release}-\text{Spontaneous Release})\times 100\%$$

The total release is determined by adding perchloric acid (3% final concentration) to target cells, and the spontaneous release is measured in the absence of antibody and effector cells.

Complement Dependent Cytotoxicity Assay [38]: NCI H82 cells are harvested at about 30-60% confluency, and washed and resuspended in a final concentration of about $5\times10^6$ cells per 1.7 mL of RPMI medium. Calcein is added to a final concentration of about 10 μM. The cells are then incubated at 37° C. in a $CO_2$ incubator. After labeling, the cells are washed twice in PBS and resuspended in pre-warmed RPMI medium to a final concentration of about $6.25\times10^4$ cells per mL. To 160 μL of the cell suspension in a well of a 96-well plate, about 20 μL of human serum and 20 μL of anti-Abn$V_2$ solution containing 0.1 to 1.0 μg of antibody are added. After incubating the cells at room temperature for about 45 min, the plate is centrifuged, and the supernatant from each well is analyzed by fluorometry to measure cell death (as measured by calcein release at 485/535 nm). Total lysis is achieved by solubilizing the cells from the control samples without the addition of the tested monoclonal antibody, by adding about 20 μL of a 9% solution of Triton X-100, with an adjustment to the increase in total volume. Spontaneous lysis is determined from control samples without the addition of the tested monoclonal antibody. All experiments are performed in triplicates. Specific lysis is determined by the following formula:

$$\%\ \text{Specific lysis}=(\text{Treated sample}-\text{Spontaneous sample})/(\text{Total lysis}-\text{Spontaneous lysis})\times 100\%$$

Preliminary results showed that antibodies to Abn$V_2$ decrease the growth of NCI H82 cells in vitro.

Example IX

Vasopressin V₂ Receptor Gene Expression and the Nature of AbnV₂

Using RT-PCR and sequencing with nested primers, it was shown that the gene for vasopressin $V_2$ receptor is expressed in all four breast cancer cell lines examined (i.e., MCF-7, ZR-71, SKBR3, and MDA-MB231).

The studies showed that breast (and ovarian) cancer cells express an abnormal mRNA message for the $V_2$ receptor that arises from alternative slicing. The abnormal mRNA contains the entire 106 bases of the intron 2 sequence of the $V_2$ receptor gene. As a result, such an abnormal mRNA, through reading of a premature stop codon, gives rise to a truncated $V_2$ receptor (also known as "AbnV$_2$") lacking the seventh trans-membrane domain. The specific C-terminal structure in AbnV$_2$ is outside the plasma membrane, and is available for targeting by antibodies.

Polyclonal antibodies to the abnormal C-terminal sequence of this receptor has been generated. Western Analysis using such antibodies showed that a protein representing the truncated receptor was present in all four cell lines examined (three estrogen-responsive and one triple-negative).

Example XI below also demonstrates that AbnV$_2$ protein is expressed at the membrane of tumor cells (see below).

Example X

AbnV₂ Expression in Breast Cancer

Figure 5:
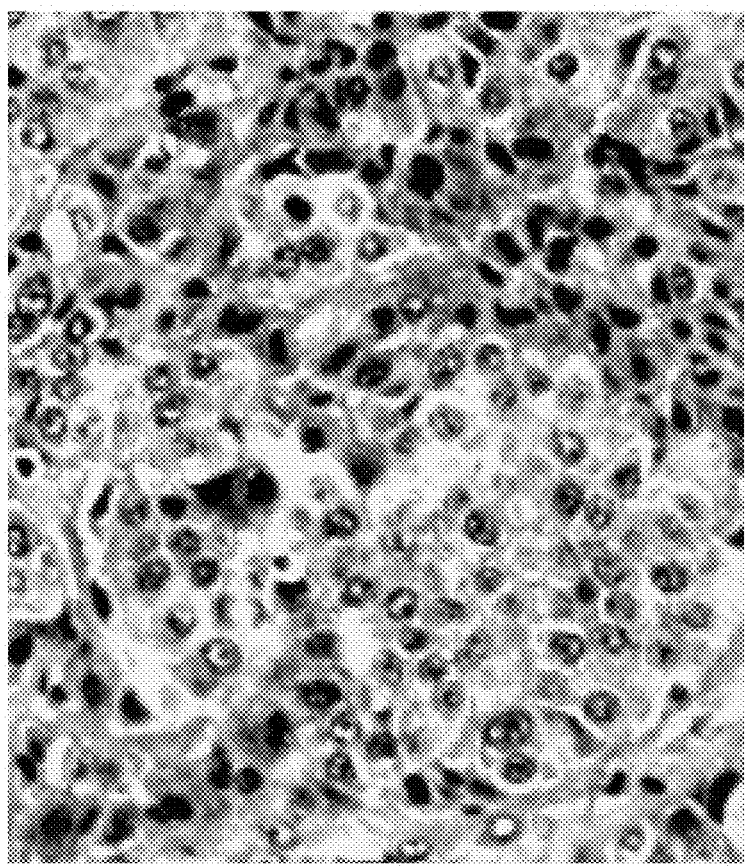
FIG. 5 is a representative IHC staining image of a breast cancer tissue with anti-AbnV$_2$ antibody.

Immunohistochemistry (IHC) has been performed on ductal and lobular breast cancer sections from 18 patients (FIG. 5), using polyclonal antibodies raised against the unique extracellular C-terminal domain of AbnV$_2$. Amidated peptide was coupled to bovine thyroglobulin as an effective antigen for generating the polyclonal antibodies in rabbits.

For IHC, the active IgG2b fraction of the antiserum was isolated using protein A Sepharose. The sABC technique of IHC, with citrate "antigen recovery," on 4 µm sections was employed (SSI System, Biogenex). As a control, excess peptide antigen was used to successfully block the primary antibody. These studies revealed the presence of AbnV$_2$ in seemingly all neoplastic cells of all tumor tissue sections. No staining was found with normal kidney, breast, liver and lung tissues.

Example XI

Figure 6:
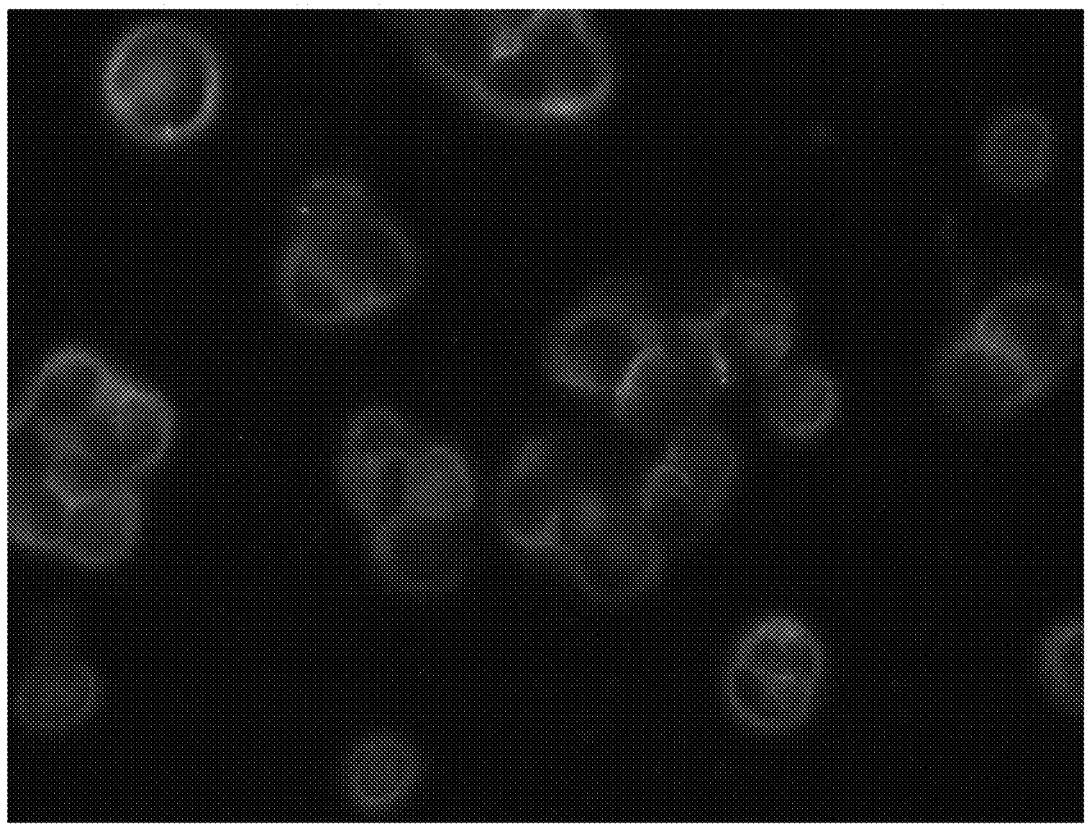
FIG. 6 is a confocal image generated by anti-AbnV$_2$ antibody staining of MCF-7 breast cancer cells.

AbnV₂ Receptor Protein is Present on the Surface of Breast Cancer Cell Lines Example IX demonstrated that the AbnV$_2$ receptor protein is present on MCF-7 and MDA-MB231 breast cancer cell lines. This was shown both by Western analysis [3*] and by confocal microscopy employing polyclonal antibodies to a unique extracellular C-terminal fragment of AbnV$_2$. FIG. 6 shows confocal image of surface fluorescent staining of the AbnV$_2$ receptor on MCF-7 cancer cells.

Example XII

Anti-AbnV₂ Antibodies Impair Ovarian Tumor Growth In Vitro

This example demonstrates that anti-AbnV$_2$ antibodies decrease the viability of ovarian cancer cells.

Ovarian cancer cells A2780 were plated in 96 well plates at $1$-$2 \times 10^4$ cells/well. The cells were incubated with PBS/glycine containing albumin (1.25 mg/mL), in the presence of different dilutions of IgG isolated Manda anti-AbnV$_2$ polyclonal antibodies, or vehicle as control. Alamar Blue was later added to each well following an incubation period. Fluorescent readings at excitation wavelength of 530-560 nm and emission wavelength of 590 nm and above were taken on a SYNERGY HT Multi Detection Reader.

Figure 7A:
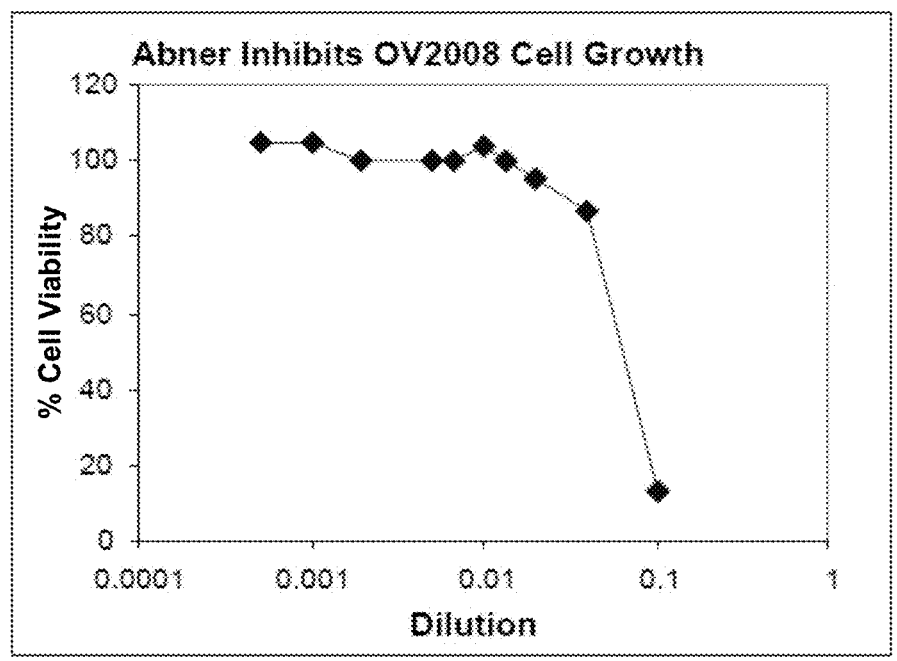
FIGS. 7A and 7B show that anti-AbnV$_2$ antibody inhibits ovarian cancer cell proliferation.
Figure 7B:
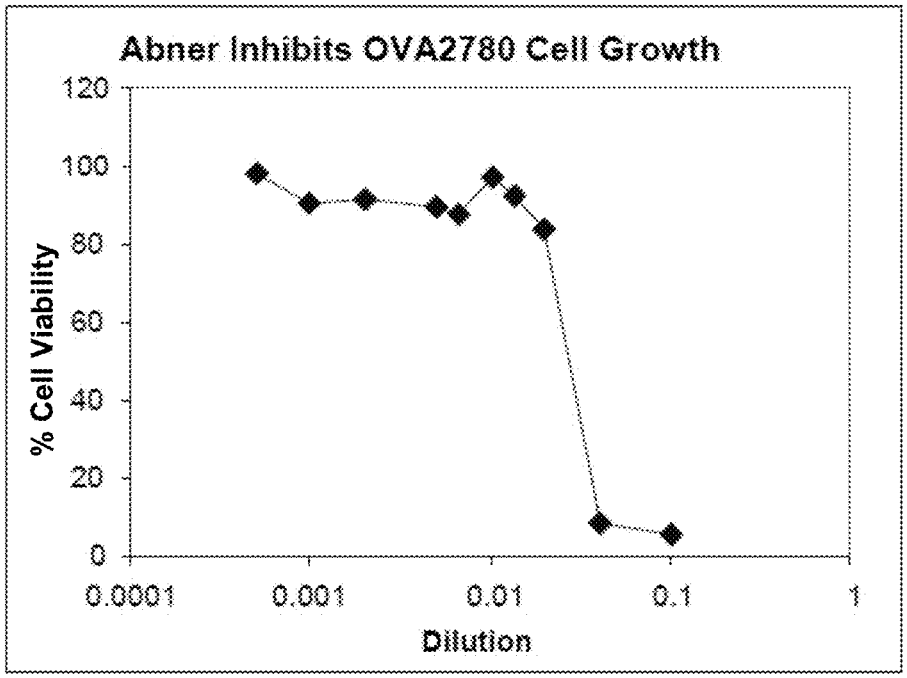

The result showed that the anti-AbnV$_2$ Ab (referred to as Abner) produced dramatic reductions in cell viability. The results were statistically significant ($p<0.001$) for tumor growth inhibition using estimated nanogram quantities of anti-AbnV$_2$ antibodies. See FIGS. 7A and 7B.

These antibodies are predicted to inhibit breast cancer cells in a similar manner.

Example XIII

Extended Treatment of Tumor Xenografts with Native (Unmodified) Anti-GRSA Monoclonal Antibodies Prevents Re-Growth GRSA is a cell surface antigen discovered by Applicants, and it is related to vasopressin expression.

Estrogen-responsive MCF-7 breast tumors and triple-negative MDA-MB231 breast tumors were growth in nu/nu mice until tumors attained sizes of approximately 0.5 cm in length.

For this study, the effect of 50 µg anti-GRSA antibody given i.p. each day for 16 days was compared to that of saline treatment. In a previous study, anti-GRSA antibody was compared to isotypic ubiquitous antibody MOPC21.

Figure 8A:
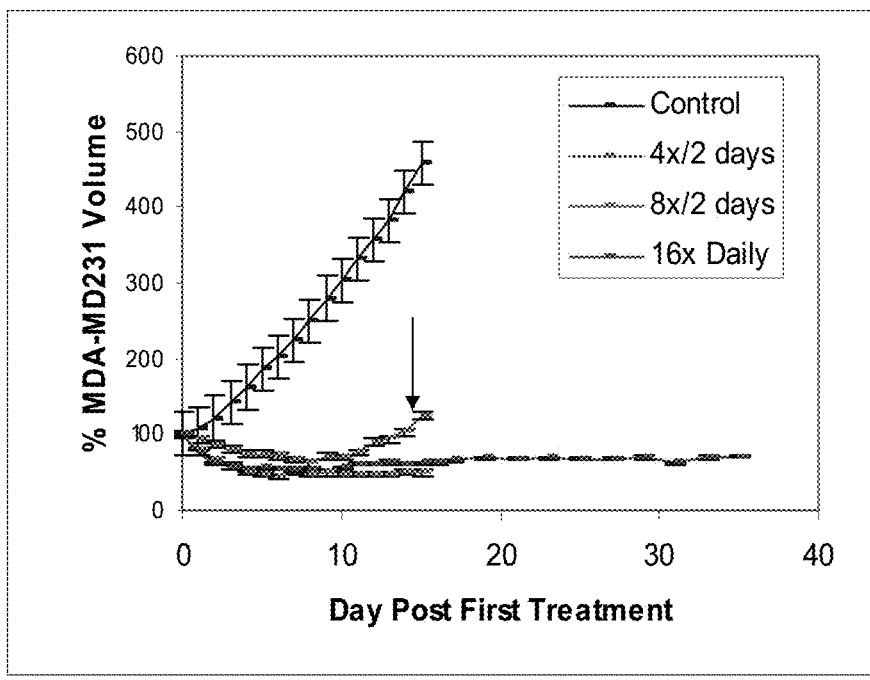
FIGS. 8A and 8B show anti-GRSA antibody daily treatment (50 µg) for 16 days shrinks and prevents re-growth of (FIG. 8A) MDA-MB-231 breast tumors, and, (FIG. 8B) MCF-7 breast tumors. Arrow denotes day of last treatment.
Figure 8B:
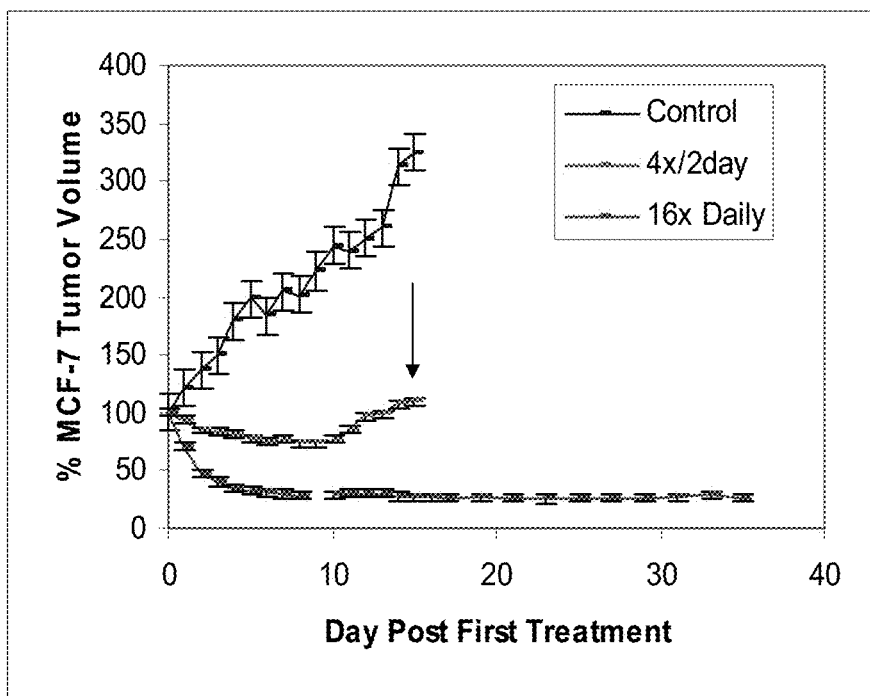
Figure 9A:
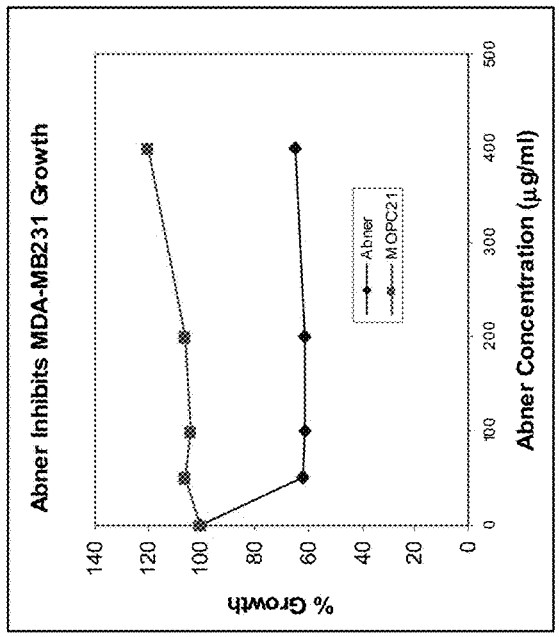
FIGS. 9A-9C show Abner anti-proliferative studies in breast cancer.
Figure 9B:
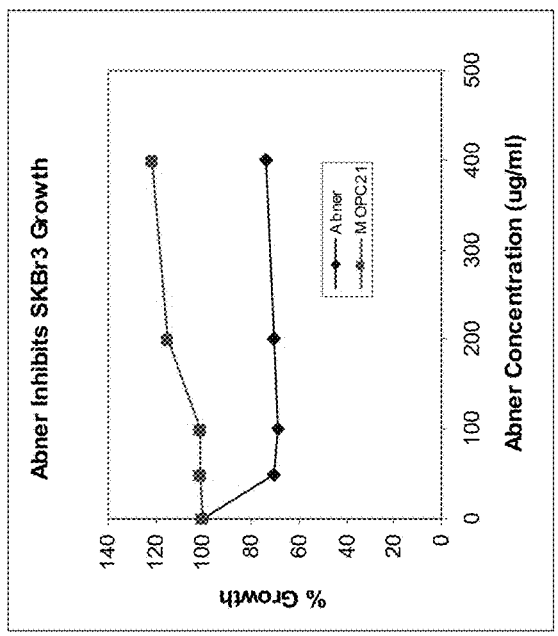
Figure 9C:
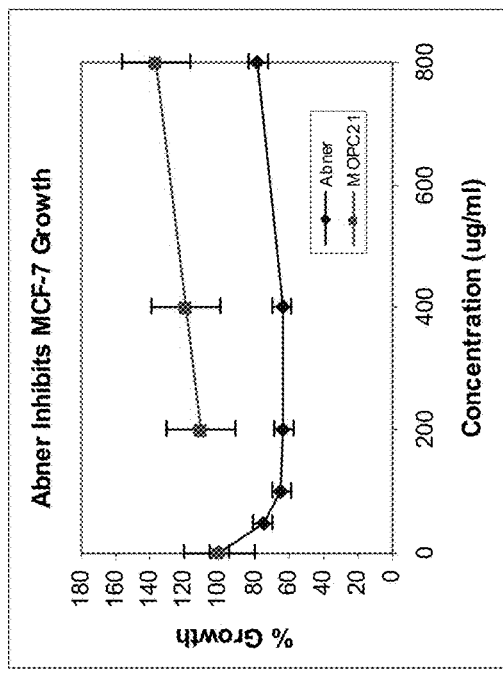
Figure 10A:
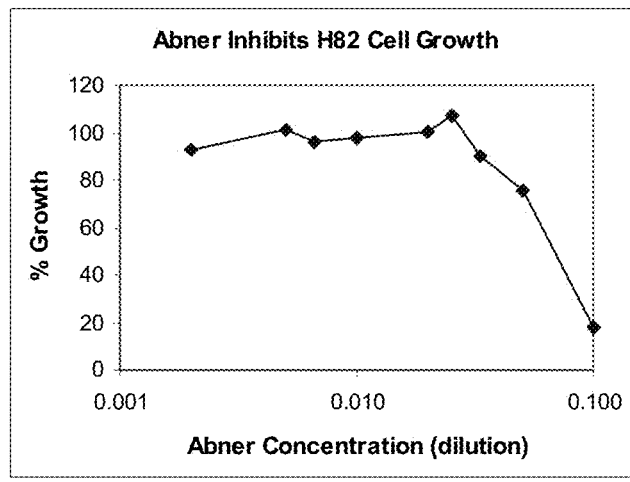
FIGS. 10A and 10B show Abner anti-proliferative studies in SCLC & ovarian cancer.
Figure 10B:
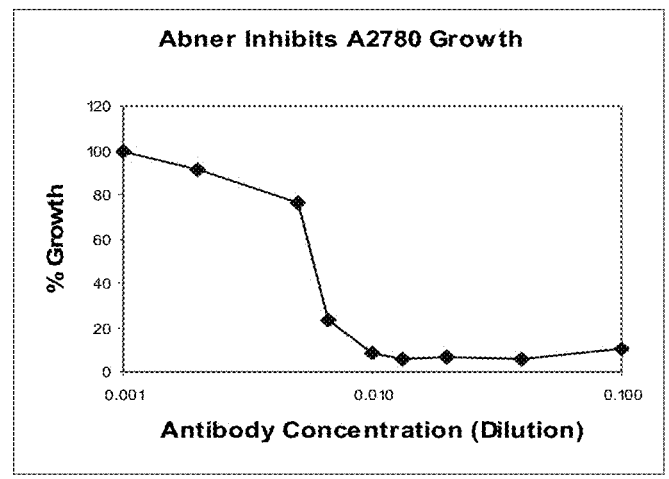
Figure 11:
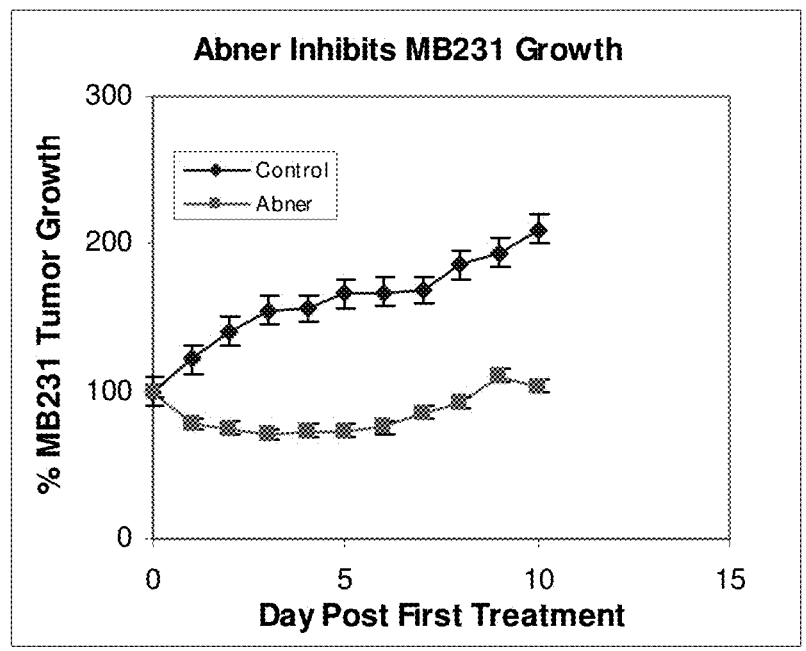
FIG. 11 shows Abner animal study result.

Tumor growth was measured daily for 20 days beyond the final treatment. Four animals were used in each group. Body weight was measured daily. At the end of the study, tumor, liver, and kidneys were examined for possible pathological changes. The results are shown in FIGS. 8A and 8B.

Anti-GRSA treatment of both MCF-7 and MDA-MB231 tumors caused, in all cases, a large shrinkage in tumor size. These tumors showed no re-growth for the first 20 days of observation following treatment. In contrast, saline treated tumors showed rapid growth, such that at Day 16, they were about 3.3 and 4.5 times their size at the start of the study. In fact, these tumors became so large (most >8000 cubic mm), that control animals had to be terminated at Day 16. Histological evaluation of normal tissues revealed no damage by extensive treatment with the anti-GRSA antibody. Meanwhile, treated tumors exhibit massive necrosis, and an estimated 75% of the tumor cells were destroyed (Data not shown). The result demonstrates the feasibility of using native anti-AbnV$_2$ Ab to treat breast tumors.

Example XIV

Treatment of Breast Tumors in Mice with Anti-AbnV₂ Monoclonal Antibodies

This study is designed to demonstrate that anti-AbnV$_2$ monoclonal antibody directed against the C-terminus of the AbnV$_2$ receptor can be used in therapy.

Dosing and treatment schedules are based on earlier studies in mice with monoclonal antibody to another marker GRSA (see Example XIII above). Both unmodified AbnV$_2$ monoclonal antibody and $^{90}$Yttrium-labelled monoclonal antibody are tested for their ability to destroy breast cancer tumor xenografts, or to cause considerable reduction in tumor size, in nu/nu mice innoculated with breast cancer cell lines.

MCF-7 (estrogen-responsive) and MDA-MB231 (triple-negative) cell lines (about $2 \times 10^7$ cells per mouse) are grown as subcutaneous tumor xenografts for 14-21 days, until tumor diameter reaches about 0.5-0.75 cm in nu/nu mice. Two studies are conducted with each cell line, one involving treatment with native (unmodified) antibody, the other with $^{90}$Yttrium-labeled antibody.

Three days before tumor treatments commences, animals with sizeable xenografts are divided into three groups (N=8 per group), and tumor sizes are measured daily.

In the first study (Day 0) of treatment, Control Group 1 will only receive PBS vehicle. Two other groups will receive eight intravenous doses each comprising 50 µg/25 gm body weight ubiquitous IgG (e.g. MOPC21) or anti-AbnV$_2$ at two day intervals.

For the second study, two groups receive 50 µCi/25 gm body weight of $^{90}$Y-labeled MOPC21 (~2 µg) with 48 µg/25 gm body weight unmodified MOPC25, or the same amount of $^{90}$Y-anti-AbnV$_2$ and unmodified anti-AbnV$_2$. Tumor size is measured in blinded fashion at daily intervals for 40 days following commencement of treatment. Body weight is measured daily for at least 40 days to evaluate toxicity. At the end of the study, brain, liver, kidney, and spinal chord are fixed, blocked, sectioned, and stained, for a review of organ toxicity by a pathologist.

It has been observed that, at 3 weeks after tumor cell implantation, breast tumors reach a size of about 1 cm in diameter, and begin to grow at a rate doubling their size every 4-7 days. A total of 96 animals are used for the four studies (2×24 for each cell line).

Statistical Considerations: This study focuses on comparing tumor growth rates for the 3 groups of mice. For each mouse, we will collect longitudinal data on the tumor size (in mm$_3$). The theory of re-growth curves [24, 25] is applied to quantify tumor re-growth and treatment effect in each group. This theory has been successfully applied and published in a series of papers with a similar tumor growth delay data analysis [see 26, 27 for references]. Three cancer treatment endpoints are used: doubling time, tumor growth delay, and cancer cell surviving fraction in vivo. The re-growth curves are estimated using the theory of mixed models with longitudinal tumor volume data. As shown in previous studies, this technique adequately reflects the notorious variation of animal response to treatment through the presence of random effects. Two types of re-growth curves are applied: double exponential curve [24] and LINEXP [25]. A total of 24 mice are used for each experiment (3 groups with 8 mice per group).

It is contemplated that higher amounts of anti-AbnV$_2$ antibodies may be used to prevent tumor growth, since the 50 µg/25 gm body weight/day dose is based on the prior anti-GRSA study that showed sufficient breast cancer growth inhibition. In addition, it is of interest that the mouse monoclonal antibody from which Herceptin was generated requires about 150 µg/25 gm bw/day to produce similar effects under similar conditions. To allow for this possibility, a range from about 50-200 µg/25 gm body weight/day may be used in pilot studies to determine the ideal concentration for anti-AbnV$_2$.

It is also contemplated that higher amounts of radioactivity might be required, although this is less likely since the levels proposed here have been used effectively by others [28] as an amount that influences tumor growth without serious side-effects.

Example XV

Evaluate AbnV$_2$ as a Tumor-Specific Marker

In this study, the incidence and abundance of AbnV$_2$ are evaluated for ductal and lobular breast tumors, DCIS, breast fibrocystic disease, and for a range of normal human tissues by IHC using a modified ABC procedure, and by RIA.

The available polyclonal antibodies and monoclonal antibodies against the unique C-terminal region of AbnV$_2$ are used for the IHC and RIA studies. Positive staining for AbnV$_2$ has already been shown by Applicants, for all eighteen examined breast tumor samples obtained from an archival library, and for all four breast cancer cell lines in culture, by IHC, RT-PCR, Western analysis, and confocal microscopy (see above). The chief source of breast tumors, DCIS, breast fibrocystic conditions, and 66 normal human tissues to be examined are commercially available microarrays. If necessary, an extensive archival library of fixed breast cancer and DCIS tissues is also available. Blocks of these tissues include both formalin and AMEX fixed preparations.

Antibodies against AbnV$_2$ are tested against arrays of normal tissues to ensure specificity and/or sufficient selectability. Polyclonal and monoclonal antibodies are purified by peptide affinity chromatography before use. The sABC technique of IHC, with or without "antigen recovery," on 4 µm sections (SSI System, Biogenex) is employed in the study. Additional sections of 10 µm can be extracted for receptor proteins/peptides, and extracts assayed using established methods of RIA [20* 21* 22*].

It has been shown in prior studies that the subject antibodies do not react with normal breast, lung, kidney, and liver tissues under the conditions used for staining. For RIA, weighed (and heated for antigen retrieval if formaldehyde-fixed) tissue sections are investigated for obtaining quantitation with RIA for AbnV$_2$, so the levels of this receptor protein can be related post hoc to prognosis. A very sensitive RIA for AbnV$_2$ has recently been developed by Applicants for easy determination of receptor quantity in tissues.

Statistical Considerations: The statistical analysis methods for this aim is designed to focus on estimating the rate of AbnV$_2$ receptor protein presence in the group of tumors studied. The rate of receptor presence is estimated as a ratio of the number of tumors positive for each receptor to the total number of tumors studied. A 95% confidence interval (CI) is constructed using exact binomial. It is expected that the actual rate of marker positivity is over 90 percent, in tumor materials from 120 patients. From each patient, the presence or absence of the marker is determined. Based on an exact test, the rate of tumor marker positivity is expected to be over 90 percent if the marker is present in 114 or more samples. The probability of making this (false positive) conclusion when the actual rate of marker positivity is 90 percent or less is at most 0.038.

Example XVI

Mechanisms of Anti-AbnV$_2$ Inhibition of Tumor Cell Growth and Survival

The studies here are designed to examine the influence the anti-AbnV$_2$ antibody has on (1) key growth promoting transduction pathways, (2) the levels of free-intracellular calcium, (3) cell viability, and (4) the expression of key proteins involved in cell growth, cell cycle, drug resistance, tumor suppression, and tumor death.

For these studies, MCF-7 and MDA-MB231 breast cancer cells are incubated with anti-AbnV$_2$ antibody for times ranging from 30 sec to 72 hours at 37° C.

Cytotoxicity and Apoptosis Assays: APOTOX-GLO™ Triplex Assay (and any one component of this triple assay) and Tunel assay [17] are used to determine cytotoxicity and apoptosis induced in MCF-7 and MDA-MB231 breast cancer cells by anti-AbnV$_2$. Employment of the Stress & Toxicity PathwayFinder PCR Array and the Apoptosis PCR Array (SABiosciences) reveal which od the 84 genes of stress and cytotoxicity, and which of the 84 genes of apoptosis, are affected by anti-AbnV$_2$ treatment. Western analysis is used to follow up specific proteins identified in the MAG-1 cytotoxic and apoptotic pathways.

Selective Knockdown of AbnV$_2$: Using manufacturer's methods, shRNA Lentiviral from Santa Cruz is employed to develop, and select out with puromycin (2 µg/mL), Vasopressin V$_2$ receptor gene knockdown stable transforms of MCF-7 and MDA-MB231 cells, with knockdown confirmed by real-time RT-PCR and Western Blotting. The influence of knockdown on anti-AbnV2 monoclonal antibody influence on cell growth is assessed with Alamar Blue, by comparing their effects with those in cells modified with lentiviral particle control. The influence of anti-AbnV$_2$ on the growth of tumors derived from these selected cell lines will also be determined (see below).

Flow Cytometry of AbnV$_2$ Dependent Effects: To analyze Ca$^{2+}$ kinetics, cells are loaded with 5 µM indo-1-AM for 45 min. at 37° C. in serum-free medium. After washing with DPBS, cells are suspended in DPBS containing CaCl$_2$ (1 mM), glucose (1 mg/mL), and BSA (1%). Loaded cells are maintained at 20° C. until flow analysis [29*] is performed on a FacStar Plus flow cytometer.

Prior to analysis, loaded cells are placed at 37° C. for 2-5 min. Fluorescence records are measured over 4 min, at excitation wavelength of 356 nm and emission wavelength of 405 nm (Ca$^{2+}$-bound indo-1-AM) and 485 nm (free-indo-1-AM). Incubating cells with EGTA-AM and administrating Ca$^{2+}$ buffer without ligand are used as negative controls. Data are analyzed using Flowjo 3.4 software.

Western Analysis of Pathways Affected by Anti-AbnV2: Adhered cells are serum starved for 12 h prior to treatment with 1-50 µg/mL anti-AbnV2 monoAb or vehicle, for 1 h, 2 h, 4 h, 24 h and 48 h. Cells are lysed in RIPA buffer, pH 7.4 and centrifuged at 10,000×g for 4 min at ambient temperature. Supernatents are then mixed with 3× Laemmli sample buffer containing 3% mercaptoethanol and heated for 5 min at 100 oC. Protein extract are subjected to 10% SDS PAGE and transferred to PVDF membranes. Blocked membranes are probed at 4 oC with Abs to recognized pathway proteins such as anti-phospho-ERK1/2, anti-ERK1/2, and anti-phospho-MEK (Cell Signal Technologies) and visualized following secondary Ab-HRP complex, and ECL reagents. For quantification, membranes are scanned) and analysed with Quantity One 4.2.1 software (BioRad).

SemiQuantitative RT-PCR and Quantitative RT-PCR: Total RNA is extracted from cells following TRIzol (GibcoBRL) treatments. The RNA is then reverse transcribed (Invitrogen) to create cDNA, which is then amplified by PCR for specific growth-related products (Superarray Technologies).

For quantitative analysis, transcription analysis kits from Superarray Technologies, in addition to the Stress & Toxicity Pathfinder PCR Array and the Apoptosis PCR Array of SABiosciences, may be used to evaluate transcription pathways, growth factors, and drug resistance, with Real-Time PCR on ICYCLER (BioRad) and quantitation with SYBR Green.

Ability of Monoclonal Antibody to Kill AbnV$_2$ Knockdown Tumors in Mice: Established techniques are used to determine if doxycycline-triggered shRNA knockdown of AbnV$_2$ reduces the growth rates of growing breast cancer tumors. In addition, any potential reduction of the effect of unmodified anti-AbnV$_2$ monoclonal antibody on tumor xenografts in nude mice of breast cancer cells, which have had their AbnV$_2$ marker knocked down by shRNA gene, is determined.

ADCC Assay: Antibody-dependent cell-mediated cytotoxicity (ADCC) of anti-AbnV$_2$ antibody on breast cancer cells, based on $^{51}$Cr release, is performed as described [30]. Briefly, breast cancer (target) cells harvested at about 30-60% confluency are labeled with $^{51}$Cr at about 100 µCi per 5×10$^5$ cells for 2 hrs. After labeling, the cells are washed extensively before use. Buffy coat cells, as effector cells, are isolated from healthy volunteers by centrifugation at 650 g for 10 minutes. The buffy coat cell counts are determined after lysing the red blood cells in 2% acetic acid. To each well of a 96-well plate, 5×10$^3$ of $^{51}$Cr-labeled H345 cells in 50 µL are added. Then, 7×10$^5$ buffy coat cells in 100 µL are added to the well, with an effector-to-target ratio of about 140:1. Then about 1 µg of anti-AbnV$_2$, or Herceptin (positive control) in about 50 µL are added to the well to a final volume of about 200 µl. The plate is then incubated at 37° C. for 4 hrs. After centrifugation, $^{51}$Cr release (as measured by cpm) in triplicates is determined. The percentage of cellular cytotoxicity is calculated using the formula below:

% Specific lysis=(Sample Count−Spontaneous Release)/(Total Release−Spontaneous Release)× 100%

The total release is determined by adding perchloric acid (3% final concentration) to target cells, and the spontaneous release is measured in the absence of antibody and effector cells.

Complement Dependent Cytotoxicity Assay [31]: Breast cancer cells are harvested at about 30-60% confluency, washed and resuspended in a final concentration of about 5×10$^6$ cells per 1.7 mL of RPMI medium. Calcein is added to a final concentration of about 10 µM. The cells are then incubated at 37° C. in a CO$_2$ incubator. After labeling, the cells are washed twice in PBS, and resuspended in pre-warmed RPMI medium to a final concentration of about 6.25×10$^4$ cells per mL. To about 160 µL of the cell suspension in a well of a 96-well plate, about 20 µL of human serum and 20 µL of anti-AbnV$_2$ solution containing about 0.1-1.0 µg of antibody are added. After incubating the cells at room temperature for about 45 min., the plate is centrifuged, and the supernatant from each well is analyzed by fluorometry to measure cell death (calcein release at 485/535 nm). Total lysis is achieved by solubilizing the cells from the control samples without the addition of the tested monoclonal antibody, by adding 20 µL of a 9% solution of Triton X-100, with an adjustment to the increase in total volume. Spontaneous lysis is determined from control samples without the addition of the tested monoclonal antibody. All experiments are performed in triplicates. Specific lysis is determined by the following formula:

% Specific lysis=(Treated sample−Spontaneous sample)/(Total lysis−Spontaneous lysis)×100%

Previous experiments have shown that the anti-AbnV$_2$ antibodies decrease the growth of ovarian cancer cells in vitro. It is expected that similar effects will be seen in breast cancer cells.

Example XVII

Inhibitory Effects of mAbner and $^{90}$Yttrium-mAbner MonoAb on NCI H82 SCLC

This experiment demonstrates that mAbner monoclonal antibody, with or without radioactive label/cytotoxic agent, inhibits tumor growth in vivo in animal model.

Mice were injected subcutaneously with 1-2×10$^7$ cells/mouse variant SCLC NCI H82 cells in the right lower flank, and tumors were allowed to grow to at least 300 mm$^3$ in size before treatment.

For one study, animals were divided into two groups (N=8 per group). Control Group 1 received only saline vehicle as treatment, while Groups 2 received daily doses of unlabeled mAbner (3 mg/kg bw) monoclonal antibody i.p. for 14 days.

Figure 13A:
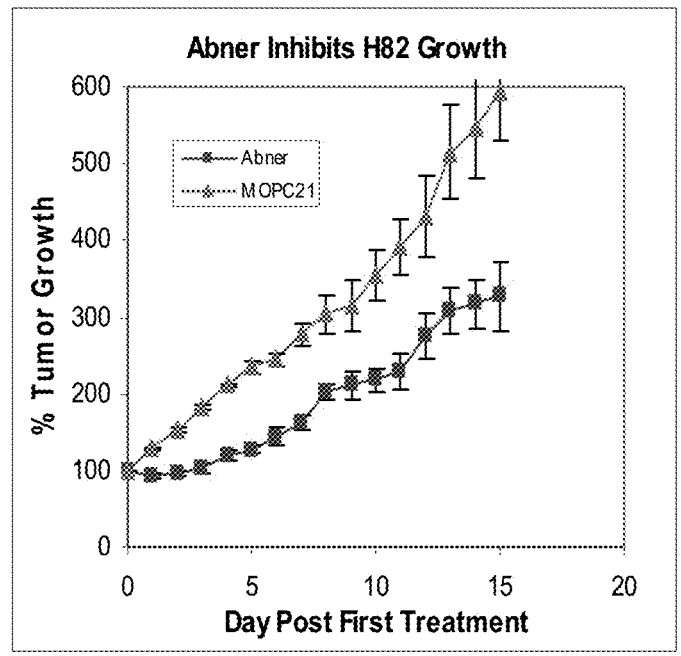
FIGS. 13A and 13B show the results of two studies of Abner (anti-AbnV2R) effects on NCI H82 Tumor Growth.
Figure 13B:
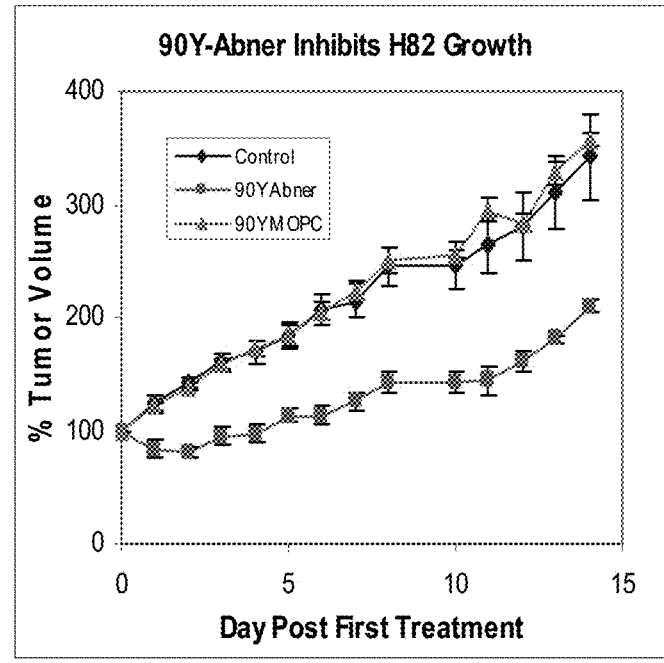

For a second study (N=8 per group), Control Group 1 comprised animals receiving saline vehicle. Group 2 received four dosing on alternate days (day 0, 2, 4, 6, 8, and 10) each of 50 µCi $^{90}$Yttrium-labeled mAbner (~5 µg) together with 3 mg/kg bw unlabeled Abner carrier. Group 3 received an identical dosing with $^{90}$Yttrium-labeled MOPC21 plus unlabeled carrier MOPC21 antibody. Tumor size was measured in semi-blinded fashion each day for 3 weeks. Results are shown in FIGS. 13A and 13B, which represent changes as a percentage of tumor size before treatment.

There was a significant effect of Abner on tumor growth, with native Abner treatment reducing growth to about only half of the rate of MOPC21 treated tumors (p<0.03), and with an almost 3-fold increase in doubling time. An initial reduction in tumor volume to ~80% occurred with Abner treatment. For the second study, $^{90}$Yttrium-labelled MOPC21 treatment produced a tumor growth curve indistinguishable from saline control, while $^{90}$Yttrium-labelled mAbner treatment reduced the growth rate of tumor to about one-third of controls for the dosing period (p<0.007). After the end of the treatment, tumor growth rate in the group previously treated by $^{90}$Yttrium-labelled mAbner increased to parallel that of the $^{90}$Yttrium-MOPC21 control group.

Meanwhile, no toxicity was observed in the liver and kidney biopsy sections in animals treated with $^{90}$Yttrium-labeled mAbner at the end of the study.

Example XVIII

Synergistic Efficacy of Abner with Chemotherapy in the Treatment of SCLC

Figure 14:
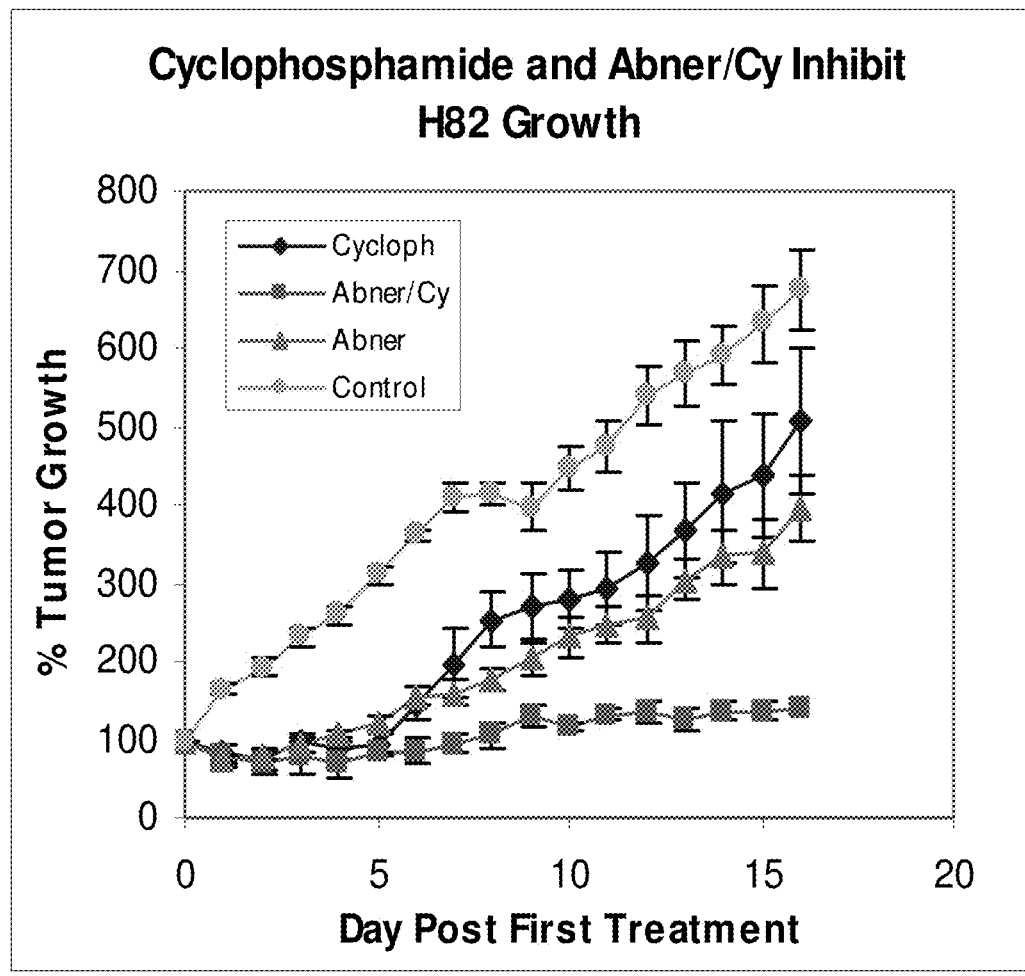
FIG. 14 shows the effect of Abner treatment on SCLC H82 xenograft growth. Treatment with saline daily for 14 days, 3 mg/kg bw Abner daily for 14 days, 50 mg/kg Cpa (cyclophosphamide) daily for three days, and Abner daily for 11 days with Cpa pretreatment.

Mice were injected subcutaneously with 1-2×10$^7$ cells/mouse variant SCLC NCI H82 cells in the right lower flank, and tumors were allowed to grow to at least 300 mm$^3$ in size before treatment. The animals were treated with saline in Group 1 animals as control, 100 µg of Abner daily per mouse for 14 days in Group 2 animals, 50 mg/kg bw of cyclophosphamide daily for 3 days in Group 3 animals, and 50 mg/kg bw of cyclophosphamide daily for 3 days followed by 100 µg of Abner daily per mouse for another 11 days in Group 4 animals. Tumor volumes were monitored daily. Tumor growth as percent of controls was shown in FIG. 14.

The data shows that treatment with either Abner or cyclosphosphamide alone inhibited tumor growth for the first 3-4 days. Thereafter, tumors in both groups started to growth, and eventually the rate of tumor growth is comparable to that of the control during the observation period. However, at the end of the study, the tumor volumes for the treated Groups 2 and 3 animals were smaller than the ones in the Control Group 1, showing the efficacy of each treatment. In contrast, increase of tumor volume in the combined therapy group was markedly reduced, so is the growth rate, demonstrating that the efficacy of the combined therapy is enhanced compared to individual treatments.

It will be apparent to those skilled in the art that various modifications and variations can be made in the present invention without departing from the scope or spirit of the invention. Other embodiments of the invention will be apparent to those skilled in the art form consideration of the specification and practice of the invention disclosed herein. It is intended that the specification and examples be considered as exemplary only, with the true scope and spirit of the invention being indicated by the following claims.

We claim:

1. A method of treating a cancer, or killing cancer cells, or inhibiting the proliferation and/or growth of cancer cells, in a patient expressing an abnormal vasopressin receptor $V_2$ (Abn$V_2$) having the amino acid sequence of SEQ ID NO: 4, said method comprising administering a therapeutically effective amount of the mouse monoclonal antibody Abner, a mouse-human chimeric monoclonal antibody thereof, a humanized monoclonal antibody thereof, or an antigen-binding portion thereof, specific for the most C-terminal six residues of SEQ ID NO: 4.

2. The method of claim 1, further comprising administering an effective amount of a pharmaceutical composition comprising a chemotherapeutic agent effective for treating the cancer.

3. The method of claim 1, wherein the cancer is small-cell lung cancer (SCLC).

4. The method of claim 1, wherein the cancer is recurrent small-cell lung cancer.

5. The method of claim 1, wherein the cancer is breast cancer.

6. The method of claim 1, wherein the cancer is ovarian cancer.

7. The method of claim 2, wherein the chemotherapeutic agent is cyclophosphamide.

8. The method of claim 1, wherein said mouse monoclonal antibody Abner, said mouse-human chimeric monoclonal antibody thereof, said humanized monoclonal antibody thereof, or said antigen-binding portion thereof, comprises a label.

9. The method of claim 8, wherein the label is selected from the group consisting of a fluorescent label, a radiolabel, a toxin, a metal compound, and biotin.

10. The method of claim 1, further comprising administering a provasopressin-binding antibody, or an antigen-binding portion thereof.

11. The method of claim 10, wherein the provasopressin-binding antibody is MAG-1.

12. A method of killing a cancer cell expressing an abnormal vasopressin receptor $V_2$ (AbnV$_2$) that has the amino acid sequence of SEQ ID NO: 4, the method comprising contacting the cancer cell with a binding agent, wherein said binding agent is the mouse monoclonal antibody Abner, a mouse-human chimeric monoclonal antibody thereof, a humanized monoclonal antibody thereof, or an antigen-binding portion thereof, specific for the most C-terminal six residues of SEQ ID NO: 4.

13. A method of inhibiting the growth of a cancer cell expressing an abnormal vasopressin receptor $V_2$ (AbnV$_2$) that has the amino acid sequence of SEQ ID NO: 4, the method comprising contacting the cancer cell with the mouse monoclonal antibody Abner, a mouse-human chimeric monoclonal antibody thereof, a humanized monoclonal antibody thereof, or an antigen-binding portion thereof, specific for the most C-terminal six residues of SEQ ID NO: 4.

* * * * *

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 1

Gly Gly Cys Ser Arg Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2
```

```
Gly Ser Thr Ser Gly
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 3

Gly Gly Ser Ser Arg Ser Ser
1               5

<210> SEQ ID NO 4
<211> LENGTH: 309
<212> TYPE: PRT
<213> ORGANISM: Artificial Sequence
<220> FEATURE:
<223> OTHER INFORMATION: Synthetic Peptide

<400> SEQUENCE: 4

Met Leu Met Ala Ser Thr Thr Ser Ala Val Pro Gly His Pro Ser Leu
1               5                   10                  15

Pro Ser Leu Pro Ser Asn Ser Ser Gln Glu Arg Pro Leu Asp Thr Arg
            20                  25                  30

Asp Pro Leu Leu Ala Arg Ala Glu Leu Ala Leu Leu Ser Ile Val Phe
        35                  40                  45

Val Ala Val Ala Leu Ser Asn Gly Leu Val Leu Ala Ala Leu Ala Arg
50                  55                  60

Arg Gly Arg Arg Gly His Trp Ala Pro Ile His Val Phe Ile Gly His
65                  70                  75                  80

Leu Cys Leu Ala Asp Leu Ala Val Ala Leu Phe Gln Val Leu Pro Gln
                85                  90                  95

Leu Ala Trp Lys Ala Thr Asp Arg Phe Arg Gly Pro Asp Ala Leu Cys
            100                 105                 110

Arg Ala Val Lys Tyr Leu Gln Met Val Gly Met Tyr Ala Ser Ser Tyr
        115                 120                 125

Met Ile Leu Ala Met Thr Leu Asp Arg His Arg Ala Ile Cys Arg Pro
130                 135                 140

Met Leu Ala Tyr Arg His Gly Ser Gly Ala His Trp Asn Arg Pro Val
145                 150                 155                 160

Leu Val Ala Trp Ala Phe Ser Leu Leu Leu Ser Leu Pro Gln Leu Phe
                165                 170                 175

Ile Phe Ala Gln Arg Asn Val Glu Gly Gly Ser Gly Val Thr Asp Cys
            180                 185                 190

Trp Ala Cys Phe Ala Glu Pro Trp Gly Arg Arg Thr Tyr Val Thr Trp
        195                 200                 205

Ile Ala Leu Met Val Phe Val Ala Pro Thr Leu Gly Ile Ala Ala Cys
210                 215                 220

Gln Val Leu Ile Phe Arg Glu Ile His Ala Ser Leu Val Pro Gly Pro
225                 230                 235                 240

Ser Glu Arg Pro Gly Gly Arg Arg Gly Arg Arg Thr Gly Ser Pro
                245                 250                 255

Gly Glu Gly Ala His Val Ser Ala Ala Val Ala Lys Thr Val Arg Met
            260                 265                 270

Thr Leu Val Ile Val Val Val Tyr Val Leu Cys Trp Ala Pro Phe Phe
```

```
                275                 280                 285
Leu Val Gln Leu Trp Ala Ala Trp Asp Pro Glu Ala Pro Leu Glu Gly
    290                 295                 300

Gly Cys Ser Arg Gly
305

<210> SEQ ID NO 5
<211> LENGTH: 1583
<212> TYPE: DNA
<213> ORGANISM: Artificial Sequence
<220> FEATURE:
<223> OTHER INFORMATION: Synthetic nucleotide

<400> SEQUENCE: 5
atgctcatgg cgtccaccac ttccggtaag gcttgcccct ccatgagtcc ggtgggcaga      60
gtgggtttga cgattcaggg aagcccctct ttctaaagac ctccttcacc ctcacctctg     120
ggtgtgtctc tccaggctgc caatgagtgg ggaggggagc acagcccac ttccccgcca      180 gggctggggc tggggctggg gctggggctg cccttccttc tggactgcat gagcctgggg     240
tgtgtatccc tcataacatg gctttcctgg agtcccctct gctaggagcc aggaagtggg     300
tgtccggatg ggggcacggg aggcaggcct gagtcccct gcacagcacc ctctctaacc      360
aggccctctt cccgactcct tcccagctgt gcctgggcat ccctctctgc ccagcctgcc     420
cagcaacagc agccaggaga ggccactgga cacccgggac ccgctgctag cccgggcgga     480
gctggcgctg ctctccatag tctttgtggc tgtggccctg agcaatggcc tggtgctggc     540
ggccctagct cggcggggcc ggcggggcca ctgggcaccc atacacgtct tcattggcca     600
cttgtgcctg gccgacctgg ccgtggctct gttccaagtg ctgccccagc tggcctggaa     660
ggccaccgac cgcttccgtg gccagatgc cctgtgtcgg gccgtgaagt atctgcagat      720
ggtgggcatg tatgcctcct cctacatgat cctggccatg acgctggacc gccaccgtgc     780
catctgccgt cccatgctgg cgtaccgcca tggaagtggg gctcactgga accggccggt     840
gctagtggct tgggccttct cgctccttct cagcctgccc cagctcttca tcttcgccca     900
gcgcaacgtg gaaggtggca gcggggtcac tgactgctgg gcctgctttg cggagccctg     960
gggccgtcgc acctatgtca cctggattgc cctgatggtg ttcgtggcac ctaccctggg    1020
tatcgccgcc tgccaggtgc tcatcttccg ggagattcat gccagtctgg tgccagggcc    1080
atcagagagg cctgggggc gccgcagggg acgccggaca ggcagcccg gtgagggagc     1140 ccacgtgtca gcagctgtgg ccaagactgt gaggatgacg ctagtgattg tggtcgtcta    1200
tgtgctgtgc tgggcaccct tcttcctggt gcagctgtgg gccgcgtggg acccggaggc    1260
acctctggaa ggtgggtgta gccgtggcta gggctgacgg ggccacttgg gcttggccgc    1320
atgcccctgt gccccaccag ccatcctgaa cccaacctag atcctccacc tccacagggg    1380 cgcccttgt gctactcatg ttgctggcca gcctcaacag ctgcaccaac ccctggatct     1440
atgcatcttt cagcagcagc gtgtcctcag agctgcgaag cttgctctgc tgtgcccggg    1500
gacgcacccc acccagcctg ggtcccaag atgagtcctg caccaccgcc agctcctccc     1560
tggccaagga cacttcatcg tga                                           1583
```